(12) United States Patent
Hamada

(10) Patent No.: US 9,672,608 B2
(45) Date of Patent: Jun. 6, 2017

(54) IMAGE PROCESSING DEVICE, ENDOSCOPE APPARATUS, IMAGE PROCESSING METHOD, AND PROGRAM

(71) Applicant: OLYMPUS CORPORATION, Tokyo (JP)

(72) Inventor: Yusuke Hamada, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/085,087

(22) Filed: Mar. 30, 2016

(65) Prior Publication Data

US 2016/0210731 A1 Jul. 21, 2016

Related U.S. Application Data

(63) Continuation-in-part of application No. 15/054,486, filed on Feb. 26, 2016, which is a continuation of
(Continued)

(30) Foreign Application Priority Data

Aug. 22, 2013 (JP) ................................ 2013-172634

(51) Int. Cl.
*H04N 5/232* (2006.01)
*G06T 5/50* (2006.01)
(Continued)

(52) U.S. Cl.
CPC .............. *G06T 5/50* (2013.01); *G06T 5/002* (2013.01); *G06T 5/003* (2013.01);
(Continued)

(58) Field of Classification Search
CPC ........................ H04N 5/23232; H04N 5/23277
(Continued)

(56) References Cited

U.S. PATENT DOCUMENTS 6,535,624 B1 3/2003 Taylor, Jr.
6,778,210 B1 8/2004 Sugahara et al.
(Continued)

FOREIGN PATENT DOCUMENTS

JP 2006-270238 A 10/2006
JP 2008-066978 A 3/2008
(Continued)

OTHER PUBLICATIONS

Office Action dated Apr. 28, 2016 received in related U.S. Appl. No. 15/054,486.
(Continued)

*Primary Examiner* — Anthony J Daniels
(74) *Attorney, Agent, or Firm* — Scully, Scott, Murphy & Presser, P.C.

(57) ABSTRACT

An image processing device includes a memory configured to store a plurality of captured images; and a processor comprising hardware, wherein the processor is configured to implement: an image selection unit configured to: select a reference image from among the plurality of captured images stored in the memory; and select candidate images to be combined with the reference image from a first group of images being captured earlier than the reference image and a second group of images being captured later than the reference image among the plurality of captured images, if the reference image is neither the earliest captured image nor the latest captured image stored in the memory, wherein; and a composition processing unit configured to compose the images to be combined selected by the image selection unit with the reference image selected by the image selection unit to generate a composite image.

7 Claims, 17 Drawing Sheets

Related U.S. Application Data application No. 14/446,829, filed on Jul. 30, 2014, now Pat. No. 9,313,403.

(51) Int. Cl.
*G06T 5/00* (2006.01)
*H04N 5/217* (2011.01)

(52) U.S. Cl.
CPC ..... *H04N 5/23254* (2013.01); *H04N 5/23277* (2013.01); *G06T 2207/10016* (2013.01); *G06T 2207/10068* (2013.01); *G06T 2207/20216* (2013.01); *G06T 2207/20221* (2013.01); *H04N 5/217* (2013.01)

(58) Field of Classification Search
USPC .................................. 348/208.99, 208.1
See application file for complete search history.

(56) References Cited

U.S. PATENT DOCUMENTS

| | | | |
|---|---|---|---|
| 7,826,730 B2 | 11/2010 | Wakamatsu et al. | |
| 2010/0253796 A1 | 10/2010 | Yano et al. | |
| 2012/0019686 A1 | 1/2012 | Manabe | |
| 2012/0120284 A1 | 5/2012 | Li et al. | |
| 2012/0274802 A1* | 11/2012 | Yamashita | H04N 5/232 348/222.1 |
| 2014/0160319 A1* | 6/2014 | Nestares | H04N 5/262 348/239 |
| 2014/0354842 A1* | 12/2014 | Pflughaupt | H04N 5/23267 348/218.1 |

FOREIGN PATENT DOCUMENTS

| | | |
|---|---|---|
| JP | 2012-023530 A | 2/2012 |
| JP | 2012-029014 A | 2/2012 |
| JP | 2012-029045 A | 2/2012 |
| JP | 2012-186593 A | 9/2012 |

OTHER PUBLICATIONS

Office Action dated Jul. 8, 2015 received in related U.S. Appl. No. 14/446,829.

Japanese Office Action dated Apr. 11, 2017 in Japanese Patent Application No. 2013-172634.

* cited by examiner

IMAGE PROCESSING DEVICE, ENDOSCOPE APPARATUS, IMAGE PROCESSING METHOD, AND PROGRAM

CROSS-REFERENCE TO RELATED APPLICATIONS

This application is a continuation-in-part application of U.S. patent application Ser. No. 15/054,486, filed on Feb. 26, 2016. The U.S. patent application Ser. No. 15/054,486 is a continuation application of a U.S. patent application Ser. No. 14/446,829, filed on Jul. 30, 2014. Priority of the U.S. patent application Ser. No. 14/446,829 is based on a Japanese Patent Application No. 2013-172634 filed on Aug. 22, 2013. In this application, the contents of the above-identified U.S. patent applications and the Japanese application are incorporated herein by reference.

BACKGROUND OF THE INVENTION

Field of the Invention

The present invention relates to an image processing device, an endoscope apparatus, an image processing method, and a program.

Description of Related Art

A method has been known which sets the image that is captured earliest as a reference image and includes using only images that are captured later than the reference image, or which sets the image that is captured latest to a reference image and includes using only images that are captured earlier than the reference image, among a plurality of images stored in a frame memory in a process of composing a plurality of images to remove noise in the time direction (for example, see Japanese Unexamined Patent Application, First Publication No. 2012-186593).

SUMMARY OF THE INVENTION

According to a first aspect of the invention, an image processing device includes a memory configured to store a plurality of captured images; and a processor comprising hardware, wherein the processor is configured to implement: an image selection unit configured to: select a reference image from among the plurality of captured images stored in the memory; and select candidate images to be combined with the reference image from a first group of images and a second group of images among the plurality of captured images, if the reference image is neither the earliest captured image nor the latest captured image stored in the memory, wherein the first group of images being captured earlier than the reference image; and the second group of images being captured later than the reference image; and a composition processing unit configured to compose the candidate images to be combined selected by the image selection unit with the reference image selected by the image selection unit to generate a composite image.

According to a second aspect of the invention, in the image processing device according to the first aspect, the image selection unit may be configured to select the candidate images to be combined with the reference image by: selecting images from the first group of images and the second group of images in order from a closest capture time to a capture time of the reference image to a farthest capture time to the capture time of the reference image, and determining whether the selected images can be used as the candidate images to be combined with the reference image in the order in which the images from the first group of images and the second group of images are selected.

According to a third aspect of the invention, in the image processing device according to the first aspect, the processor may be further configured to implement: a movement amount estimation unit configured to estimate an amount of movement of an object in one or more images among the plurality of captured images, wherein the image selection unit is configured to select the reference image based on the amount of movement estimated by the movement amount estimation unit.

According to a fourth aspect of the invention, in the image processing device according to the third aspect, the image selection unit may be further configured to select an image in which the estimated amount of movement is the minimum as the reference image.

According to a fifth aspect of the invention, in the image processing device according to the second aspect, the image selection unit may be further configured to: end selecting the candidate images to be combined with the reference image if the number of counted images reaches the number of images required to be combined with the reference image.

According to a sixth aspect of the invention, in the image processing device according to the second aspect, the image selection unit may be further configured to: end the selecting of candidate images to be combined with the reference image if it is determined that the predetermined number of consecutive images are not selected as the candidate images to be combined with the reference image during the process of determining whether the selected images are used as the candidate images to be combined.

According to a seventh aspect of the invention, an image processing method that composes a plurality of images stored in a memory to generate a composite image includes a step of selecting a reference image used as a reference for compositing the composite image from among the plurality of images stored in the memory; a step of selecting candidate images to be combined with the reference image from a group of images which are captured earlier than the reference image and another group of images which are captured later than the reference image among the plurality of images, if the reference image is neither the earliest captured image nor the latest captured image among the plurality of images stored in the memory; and a step of composing the candidate images to be combined which are selected in the step of selecting candidate images to be combined, with the reference image which is selected in the step of selecting a reference image, to generate the composite image.

According to an eighth aspect of the invention, in the image processing method according to the seventh aspect, in the step of selecting candidate images to be combined with the reference image, it may be determined whether the images selected from the plurality of images stored in the memory are used as the candidate images to be combined with the reference image, in order from a closest capture time to a capture time of the reference image to a farthest capture time to the capture time of the reference image.

According to a ninth aspect of the invention, a computer-readable device storing a program causing a computer to perform a step of selecting a reference image used as a reference for compositing the composite image from among the plurality of images stored in the memory; a step of selecting images to be combined with the reference image from a group of images which are captured earlier than the reference image and another group of images which are captured later than the reference image among the plurality of images, if the reference image is neither the earliest captured image nor the latest captured image among the plurality of images stored in the memory; and a step of composing the images to be combined, which are selected in the step of selecting images to be combined, with the reference image, which is selected in the step of selecting a reference image, to generate the composite image.

DETAILED DESCRIPTION OF THE INVENTION (First Embodiment)

Figure 1:
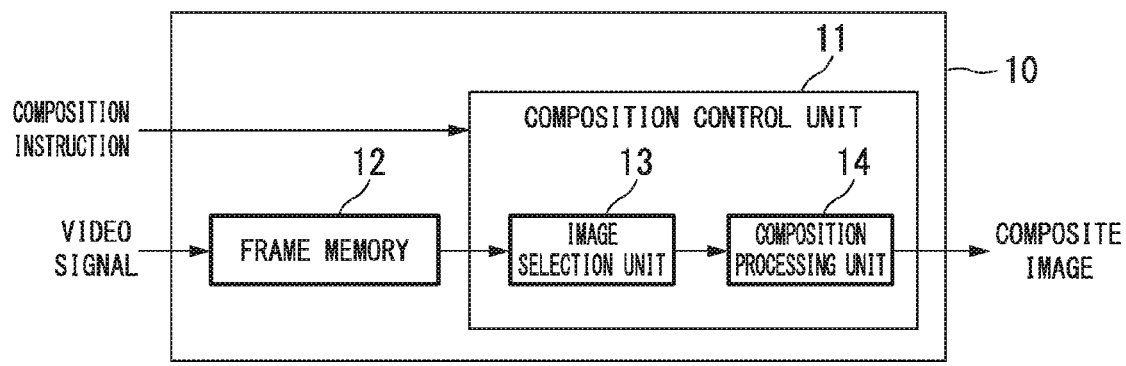
FIG. 1 is a block diagram illustrating the structure of an image processing device according to a first embodiment.

Hereinafter, a first embodiment of the invention will be described with reference to the drawings. FIG. 1 is a block diagram illustrating the structure of an image processing device 10 according to this embodiment. In FIG. 1, the image processing device 10 includes a composition control unit 11 and a frame memory (memory) 12. The composition control unit 11 includes an image selection unit 13 and a composition processing unit 14 and generates a composite image. The frame memory 12 stores input video signals (a plurality of captured images). The video signal is, for example, a moving image and includes frames which are continuously captured.

When a composition instruction is input, the image selection unit 13 selects a reference image, which is a standard for composition, and a plurality of images to be combined (to be composed) with the reference image from the frames included in the video signal which is stored in the frame memory 12. The composition processing unit 14 composes the reference image selected by the image selection unit 13 with the images to be combined to generate a composite image. The composite image generated by the composition processing unit 14 is an image obtained by removing noise in a time direction from the reference image. That is, the composition processing unit 14 composes the images to be combined with the reference image to remove noise from the reference image.

Figure 2:
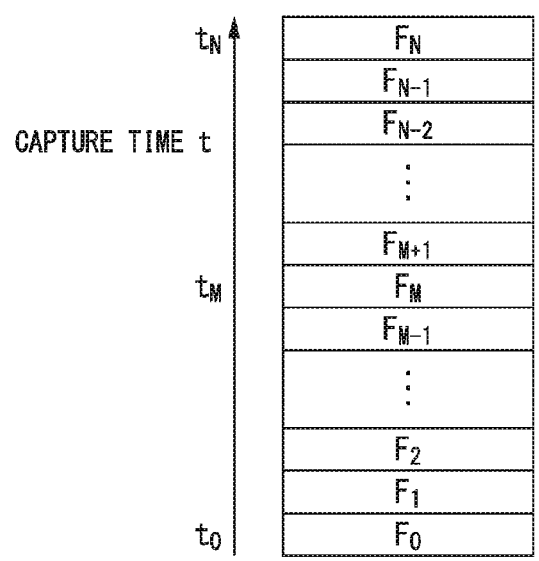
FIG. 2 is a schematic diagram illustrating an example of frames stored in a frame memory in the first embodiment.

Next, an example of the frames stored in the frame memory 12 will be described. FIG. 2 is a schematic diagram illustrating an example of the frames stored in the frame memory 12 in this embodiment. In FIG. 2, the frame memory 12 stores N frames $F_0, F_1, F_2, \ldots, F_{M-1}, F_M, F_{M+1}, F_{N-2}, F_{N-1}, F_N$ with different capture times t (N is a natural number and M is an integer that is equal to or greater than 0 and equal to or less than N). In addition, in FIG. 2, the frames are captured in the order of the frame $F_0$ to the frame $F_N$, the frame $F_0$ is captured earliest, and the frame $F_N$ is captured latest. For example, the frame $F_0$ is captured at $t_0$ and the frame $F_1$ is captured at $t_1$. The other frames $F_2$ to $F_N$ are captured at $t_2$ to $t_N$, respectively.

Figure 3:
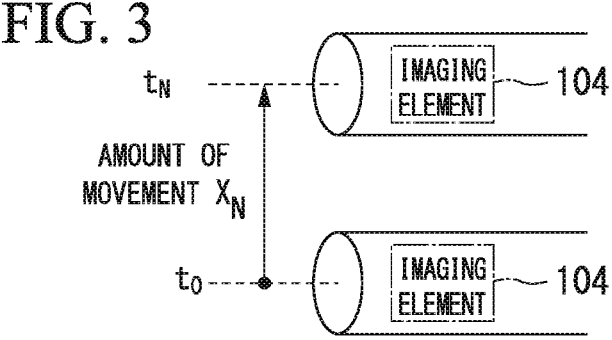
FIG. 3 is a schematic diagram illustrating the relationship between the time when an imaging element captures an image and the position of the imaging element in the first embodiment.

Next, the video signal input to the frame memory 12 will be described. For example, a video signal which is captured by an imaging element provided at the tip of an endoscope apparatus is input to the frame memory 12. FIG. 3 is a schematic diagram illustrating the relationship between the time when an imaging element 104 provided at the tip of the endoscope apparatus captures an image and the position of the imaging element 104. In FIG. 3, the imaging element 104 captures the image of an object for the period from the time $t_0$ to the time $t_N$. Then, the imaging element 104 outputs the frame $F_0$ at the time $t_0$ and outputs the frame $F_N$ at the time $T_N$ (see FIG. 2). In addition, the position of the imaging element 104 is different at the time $t_0$ and the time $t_N$. In FIG. 3, the amount of movement X of the imaging element 104 between the imaging element 104 at the time $t_0$ and the imaging element 104 at the time $t_N$ is $X_N$.

When the object remains stationary, the position of the object in the frame $F_0$ is different from the position of the object in the frame $F_N$ since the imaging element 104 is being moved. Therefore, when the frame $F_0$ and the frame $F_N$ are composed with each other to generate a composite image, a composition process needs to be performed after positioning is performed such that the position of the object in the frame $F_0$ and the position of the object in the frame $F_N$ are aligned with each other.

Figure 4A:
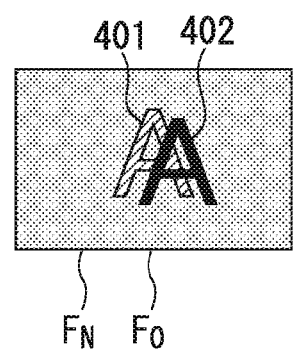
FIG. 4A is a schematic diagram illustrating the procedure of a process according to the related art which composes a frame $F_0$ and a frame $F_N$ to generate a composite image.
Figure 4B:
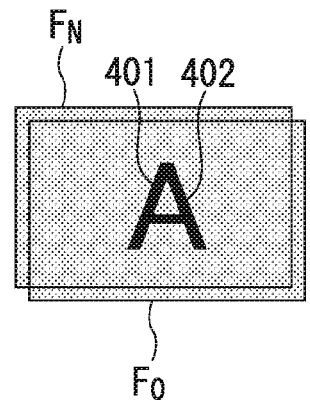
FIG. 4B is a schematic diagram illustrating the procedure of the process according to the related art which composes the frame $F_0$ and the frame $F_N$ to generate the composite image.
Figure 4C:
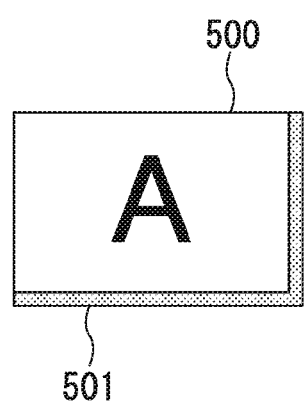
FIG. 4C is a schematic diagram illustrating the procedure of the process according to the related art which composes the frame $F_0$ and the frame $F_N$ to generate the composite image.

FIGS. 4A to 4C are schematic diagrams illustrating the procedure of the known process of composing the frame $F_0$ and the frame $F_N$ to generate a composite image. In FIGS. 4A to 4C, the frame $F_0$ output from the imaging element 104 shown in FIG. 3 is the reference image and the frame $F_N$ is the images to be combined (see the frames shown in FIG. 2). In addition, a letter "A" is captured as the object. The frame $F_0$ and the frame $F_N$ each include noise.

FIG. 4A is a schematic diagram illustrating a superimposed image of the frame $F_0$ and the frame $F_N$. The position of the imaging element 104 is different at the time $t_0$ when the frame $F_0$ is captured and at the time $t_N$ when the frame $F_N$ is captured. Therefore, in FIG. 4A, the deviation between the position of an object "A" 401 in the frame $F_0$ and the position of an object "A" 402 in the frame $F_N$ is the amount of movement $X_N$. The positional deviation between the object "A" in the images to be combined (frame $F_N$) and the object "A" in the reference image (frame $F_0$) is referred to as the amount of blur.

FIG. 4B is a schematic diagram illustrating two frames, with the position of the object "A" in the frame $F_N$ being aligned with the position of the object "A" in the frame $F_0$. In FIG. 4A, the composition processing unit 14 aligns the position of the object "A" 402 in the frame $F_N$, which is the images to be combined, with the position of the object "A" 401 in the frame $F_0$ that is the reference image. As such, when the object is positioned in order to move the position of the frame $F_N$, a region in which the frame $F_0$ and the frame $F_N$ overlap each other and a region in which the frame $F_0$ and the frame $F_N$ do not overlap each other are generated.

FIG. 4C is a schematic diagram illustrating a composite image 500 generated by calculating the weighted average of the frame $F_0$ and the frame $F_N$ which are positioned relative to each other. The region of the composite image 500 is the same as the region of the frame $F_0$ which is the reference image. In FIG. 4C, noise is reduced in the region in which the frame $F_0$ and the frame $F_N$ overlap each other. However, since the composite image 500 is generated by calculating the weighted average of the frame $F_0$ and the frame $F_N$, the brightness of a region 501 in which the frame $F_0$ and the frame $F_N$ do not overlap each other is low.

Therefore, the maximum amount of blur of the images to be combined is determined according to the allowable region 501. For example, when the size of the allowable region 501 is widened, because the images to be combined with a large amount of blur are used to generate the composite image 500, it is possible to use a large number of frames. Accordingly, although it is possible to improve a noise reduction effect, the effective size of the image without reduced brightness is small. When the allowable region 501 is narrowed, because it is difficult to use the images to be combined with a large amount of blur to generate the composite image 500, the composite image is small. Consequently, the noise reduction effect is reduced, but the effective size without reduced brightness is large. In accordance with these things, the maximum amount of blur is decided. When the amount of movement $X_N$ of the imaging element 104 is large, the amount of blur of the images to be combined is large. Therefore, the allowable amount of movement $X_N$ of the imaging element 104 is determined on the basis of the allowable range of the region 501.

Next, the relationship among the reference image, the allowable amount of movement X per unit time of the imaging element 104, and the allowable range which is selected as the images to be combined will be described.

Figure 5:
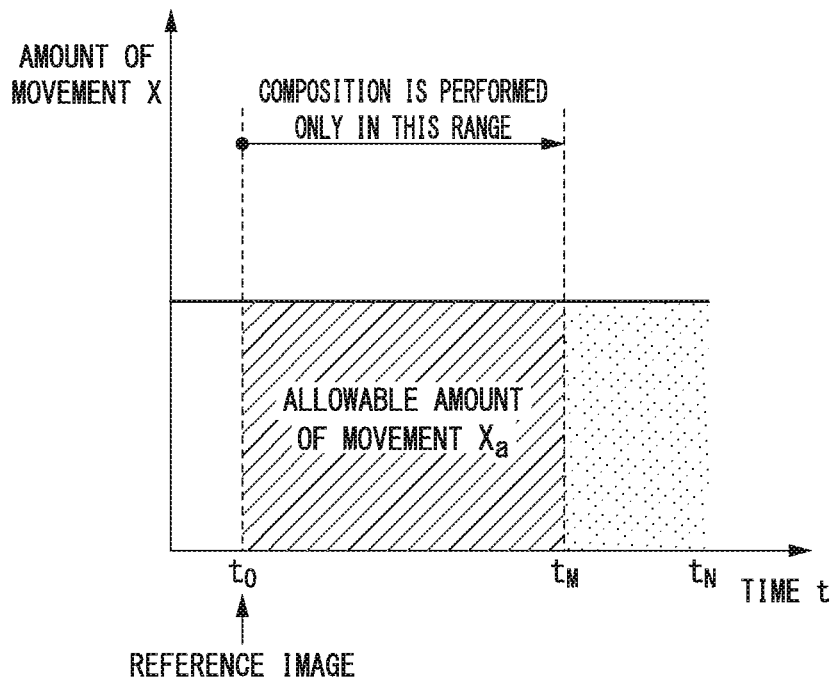
FIG. 5 is a graph illustrating the allowable amount of movement X of the imaging element when the frame $F_0$ which is captured at a time $t_0$ is used as a reference image in the first embodiment.

FIG. 5 is a graph illustrating the allowable amount of movement X per unit time of the imaging element 104 when the oldest frame $F_0$ which is captured at the time $t_0$ among a plurality of frames stored in the frame memory 12 is set as the reference image. In the graph of FIG. 5, the vertical axis indicates the amount of movement per unit time of the imaging element 104 and when the interval between captured frames is constant, the amount of movement per unit time of the imaging element 104 is regarded as the amount of movement per between frames. Hereinafter, the allowable amount of movement X per unit time of the imaging element 104 is simply referred to as the amount of movement X. The horizontal axis of the graph of FIG. 5 indicates a time t. In addition, the imaging element 104 moves in a straight line with a constant speed. The allowable amount of movement X of the imaging element 104 is referred to as $X_a$.

In FIG. 5, the amount of movement X of the imaging element 104 is more than the amount of movement $X_a$ at a time after a past time $t_M$. Therefore, the frames F which can be used as the images to be combined to generate the composite image 500 are the frames $F_0$ to $F_M$ which are captured for the period from the time $t_0$ to the time $t_M$ (see FIG. 2). That is, when the frame $F_0$ is set as the reference image, it is difficult to use the frames $F_{M+1}$ to $F_N$ which are captured at the times after the time $t_M$ as the images to be combined.

Figure 6:
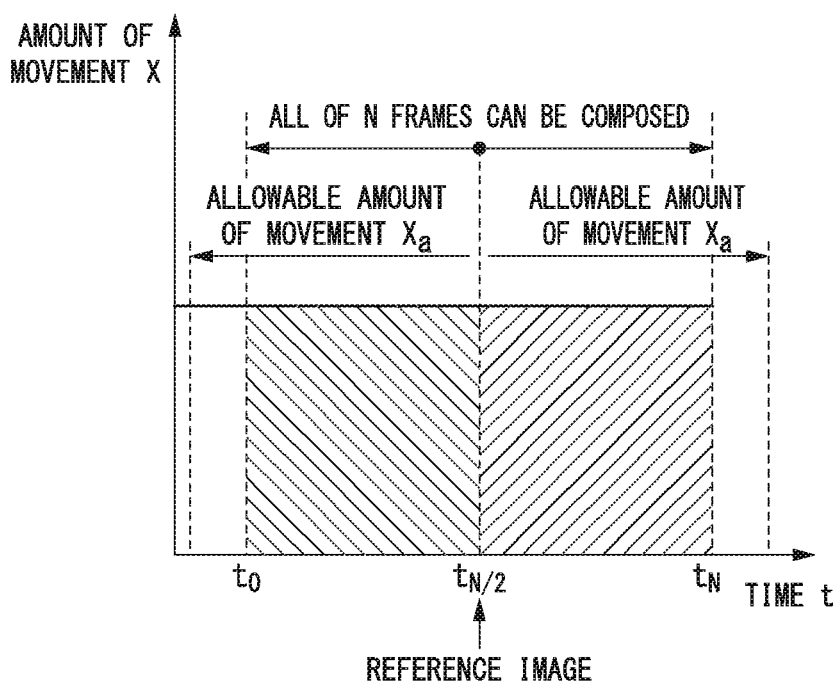
FIG. 6 is a graph illustrating the allowable amount of movement X of the imaging element when a frame $F_{N/2}$ which is captured at a time $t_{N/2}$ is used as the reference image in the first embodiment.

FIG. 6 is a graph illustrating the allowable amount of movement X of the imaging element 104 when the frame $F_{N/2}$ which is captured at a time $t_{N/2}$ is used as the reference image in this embodiment. In the graph of FIG. 6, the vertical axis, the horizontal axis, and the allowable amount of movement $X_a$ of the imaging element 104 are the same as those in the graph of FIG. 5.

In this embodiment, as the reference image, a frame is selected from the frames other than the oldest frame $F_0$ which is captured at the time $t_0$ and the newest frame $F_N$ which is captured at the time $t_N$ in the frame memory 12. Specifically, a frame $F_{N/2}$ which is captured at a time $t_{N/2}$ closest to an intermediate (middle) time between the time when the frame $F_0$ is captured and the time when the frame $F_N$ is captured is selected as the reference image.

In FIG. 6, when the frame $F_{N/2}$ captured at the time $t_{N/2}$ is set to the reference image, both the position of the imaging element 104 at the time $t_{N/2}$ when the reference image is captured and the amount of movement X based on the position of the imaging element 104 at the time $t_0$ are not more than the amount of movement $X_a$. Both the position of the imaging element 104 at the time $t_{N/2}$ when the reference image is captured and the amount of movement X based on the position of the imaging element 104 at the time $t_N$ are not more than the amount of movement $X_a$. Therefore, when the composite image 500 is generated, all of the frames before the frame $F_{N/2}$, which is the reference image, and all of the frames after the frame $F_{N/2}$, which is the reference image, can be used as the images to be combined. That is, all of the frames $F_0$ to $F_N$ captured from the time $t_0$ to the time $t_N$ can be used as the images to be combined.

As such, since the frame $F_{N/2}$ which is captured at the time closest to the intermediate time $t_{N/2}$ between the capture time $t_0$ of the oldest frame $F_0$ and the capture time $t_N$ of the newest frame $F_N$ is used as the reference image among a plurality of frames that is stored in the frame memory 12, it is possible to use a large number of frames stored in the frame memory 12 as the images to be combined. Therefore, a good noise reduction effect is expected by the composition of a large number of frames. In particular, since the images to be combined is selected from a group of the frames which are captured earlier than the reference image and a group of the frames which are captured later than the reference image in the frame memory 12, it is possible to use a large number of frames as the images to be combined.

In this embodiment, the frame $F_{N/2}$ captured at the time closest to the time $t_{N/2}$ is used as the reference image. However, the invention is not limited thereto. The reference image may be selected from the frames other than the oldest frame $F_0$ which is captured at the time $t_0$ and the newest frame $F_N$ which is captured at the time $t_N$ in the frame memory 12.

Figure 7:
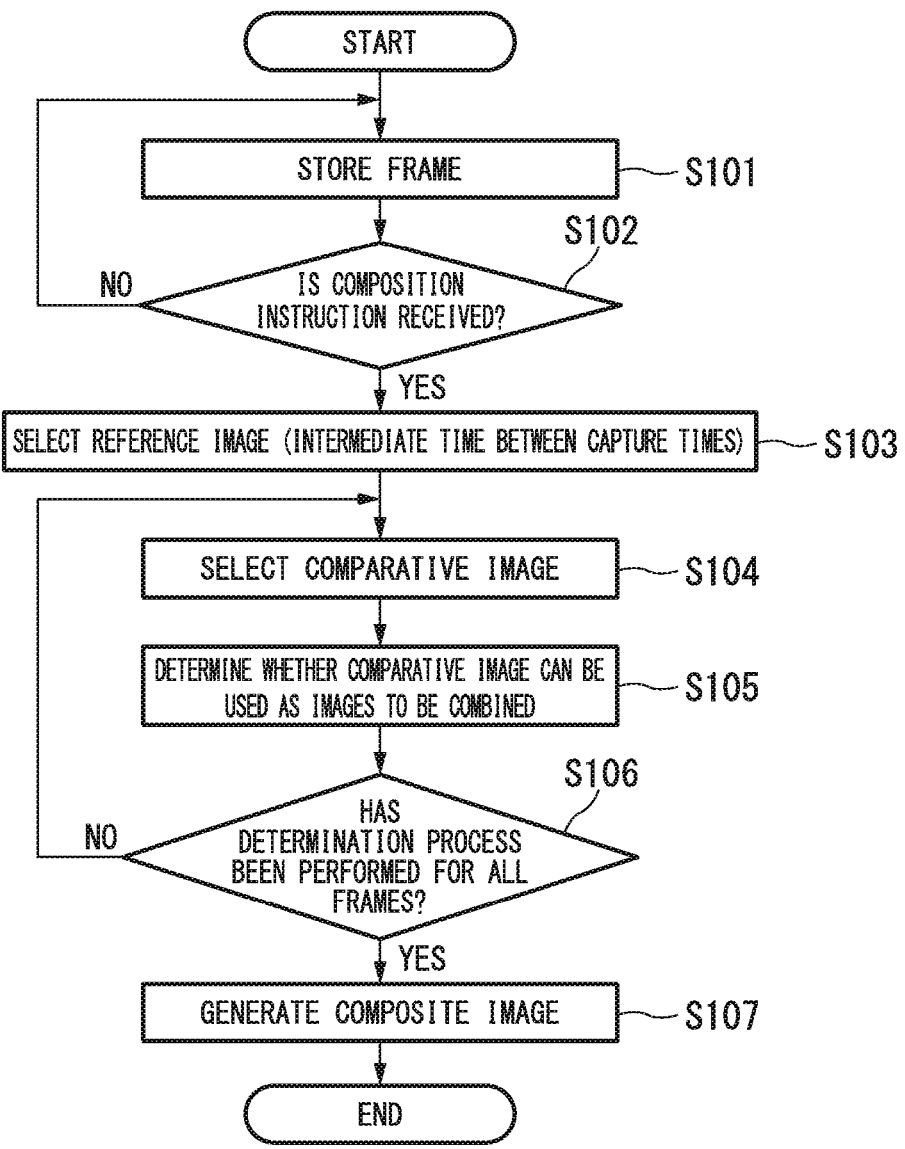
FIG. 7 is a flowchart illustrating a composite image generation process of the image processing device according to the first embodiment.

Next, a composite image generation process of the image processing device 10 will be described. FIG. 7 is a flowchart illustrating the composite image generation process of the image processing device 10 in this embodiment. In this embodiment, the frames are input one by one from the outside to the frame memory 12.

(Step S101) The image processing device 10 stores the input frames (video signals) in the frame memory 12. Then, the process proceeds to Step S102.

(Step S102) The composition control unit 11 determines whether a composition instruction is received. When the composition control unit 11 determines that the composition instruction is received, the process proceeds to Step S103. In the other cases, the process returns to Step S101. In the following description, it is assumed that the frame memory 12 stores a plurality of frames.

(Step S103) First, the image selection unit 13 selects the reference image from a group of the frames other than the frame which is captured earliest and the frame $F_N$ which is captured latest among a plurality of frames which the image processing device 10 stores in the frame memory 12. In this embodiment, the frame which is captured at the time closest to the intermediate time between the capture time of the oldest frame and the capture time of newest the frame is selected as the reference image. Then, the process proceeds to Step S104.

(Step S104) The image selection unit 13 selects, as a comparative image, one frame which is captured at the time closest to the capture time of the frame selected as the reference image from a plurality of frames other than the frame selected as the reference image. The comparative image is images to be combined candidate when the images to be combined are selected. Then, the process proceeds to Step S105. When Step S104 is performed again after Step S106, the image selection unit 13 selects one frame which is captured at the time closest to the capture time of the frame selected as the reference image from the frames which have not been subjected to the determination process in Step S105. In addition, the image selection unit 13 sequentially selects the reference image from the frame which is captured earlier than the reference image and the frame which is captured later than the reference image.

(Step S105) The image selection unit 13 determines whether the frame which is selected as the comparative image in Step S104 can be used as the images to be combined. The image selection unit 13 sets, as the images to be combined, the frame which is determined to be used as the images to be combined. Then, the process proceeds to Step S106. The image selection unit 13 determines whether the selected frame can be used as the images to be combined using, for example, the following method. The image selection unit 13 aligns the position of the object in the reference image and the position of the object in the comparative image. The image selection unit 13 calculates the amount of blur of the object in the comparative image with respect to the object in the reference image. When the calculated amount of blur is less than a threshold value, the image selection unit 13 determines that the selected frame can be used as the images to be combined. The image selection unit 13 set the frame which is determined to be capable of being used as the images to be combined. On the other hand, when the calculated amount of blur is equal to or greater than the threshold value, the image selection unit 13 determines that it is difficult to use the selected frame as the images to be combined. The threshold value is set based on, for example, the allowable range of the region 501 shown in FIG. 4C. In addition, the threshold value may be predetermined or it may be arbitrarily set.

(Step S106) The image selection unit 13 determines whether the determination process in Step S105 has been performed for all frames other than the frame which is selected as the reference image among the frames stored in the frame memory 12. When the image selection unit 13 determines that the process in Step S105 has been performed for all frames other than the frame selected as the reference image, the process proceeds to Step S107. In the other cases, the process returns to Step S104.

(Step S107) The composition processing unit 14 composes all of the images to be combined set in Step S105 with the reference image selected in Step S103 to generate a composite image. Then, the process ends.

As described above, in this embodiment, the image selection unit 13 selects, as the reference image, the frame which is captured at the time closest to the intermediate time between the capture time of the oldest frame and the capture time of the newest frame among the plurality of frames stored in the frame memory 12. In addition, the image selection unit 13 can select the frame as the comparative image from a group of the frames which are captured earlier than the reference image and a group of the frames which are captured later than the reference image. Then, the image selection unit 13 sets, as the images to be combined, the frame which can be used as the images to be combined among the frames which are selected as the comparative images. That is, the image selection unit 13 can select the frame as the images to be combined from a group of the frames which are captured earlier than the reference image and a group of the frames which are captured later than the reference image. Therefore, according to this embodiment, the image processing device 10 can generate a composite image, using a large number of frames which the image processing device 10 stores in the frame memory 12 as the images to be combined. As a result, a good noise reduction effect is expected.

In this embodiment, as a preferred example in which the reference image is selected from the frames other than the oldest frame $F_0$ which is captured at the time $t_0$ and the newest frame $F_N$ which is captured at the time $t_N$ in the frame memory 12, the frame which is captured at the time closest to the intermediate time between the capture time of the oldest frame and the capture time of the newest frame among the plurality of frames stored in the frame memory 12 is selected as the reference image. However, the invention is not limited thereto. For example, the reference image may be selected such that the number of frames which are captured earlier than the frame set as the reference image and are then stored is close to, preferably, equal to the number of frames which are captured later than the frame set as the reference image and are then stored.

In the above-mentioned example, the image selection unit 13 selects all frames (except for the reference image) stored in the frame memory 12, sets the selected frames as the comparative images, and determines whether all of the comparative images can be used as the images to be combined. However, the invention is not limited thereto. For example, the number of images to be combined may be predetermined. In this case, in Step S106, the number of reference frames which are set as the images to be combined is counted and it is determined whether the count result reaches a predetermined number of images to be combined. Even when there is a comparative image which has not been subjected to the process of determining whether the comparative image can be used as the images to be combined, the process may proceed to Step S107 at the time the number of reference frames which are set as the images to be combined reaches a predetermined value.

As such, when the number of images to be combined is predetermined, the comparative image is sequentially selected from the frame which is captured at a time close to the time when the reference image is captured, which is advantageous in improving the efficiency of the composition process in the next stage. The comparative image which is captured at a time close to the time when the reference image is captured is very likely to have a small amount of blur with respect to the reference image. Therefore, the set images to be combined is very likely to be preferentially set from the frame which has a small amount of blur with respect to the reference image. As a result, it is possible to generate a composite image with high efficiency.

(Second Embodiment)

Next, a second embodiment of the invention will be described with reference to the drawings. In this embodiment, a reference image is selected on the basis of the amount of movement of the object to be estimated by a movement amount estimation unit 21, which will be described below.

Figure 8:
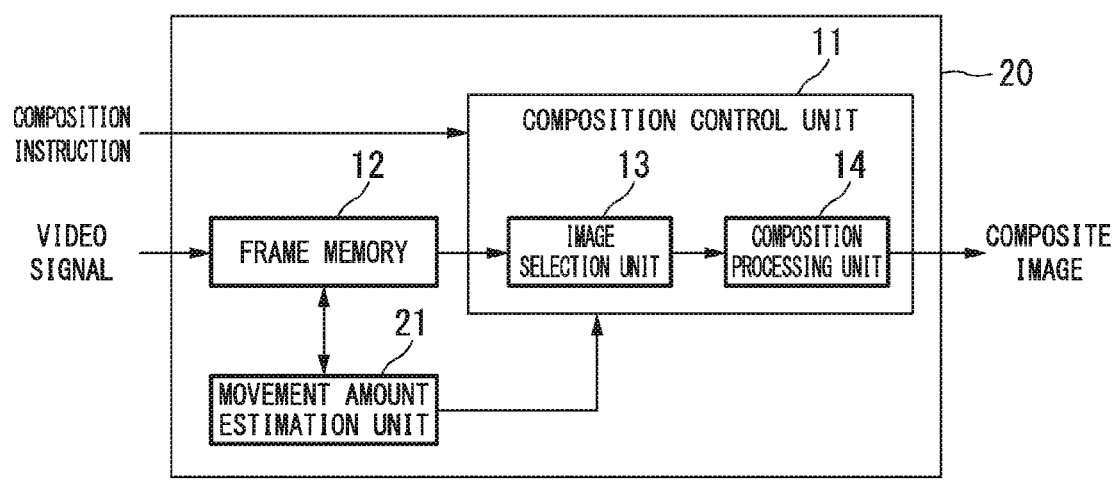
FIG. 8 is a block diagram illustrating the structure of an image processing device according to a second embodiment.

FIG. 8 is a block diagram illustrating the structure an image processing device 20 according to this embodiment. In FIG. 8, the image processing device 20 includes a composition control unit 11, a frame memory 12, and the movement amount estimation unit 21. The composition control unit 11 and the frame memory 12 are the same as those in the first embodiment. The movement amount estimation unit 21 estimates the amount of movement X of the object. There are some methods of estimating the amount of movement of the object. For example, the following methods are considered: a method which compares the brightness value of a newly input frame with the brightness value of a previously input frame to estimate the amount of movement of the object in the newly input frame; and a method which detects the amount of movement X of the imaging element 104 using a sensor in an environment in which the object hardly moves and regards the detected amount of movement X of the imaging element as the amount of movement of the object. In this embodiment, the movement amount estimation unit 21 may use any estimation method.

In this embodiment, frame processing has been described. However, when interlaced processing is performed, the amount of movement X of the object may be estimated using a newly input interlace image and an interpolated image based on a previously input interlace image.

Figure 9:
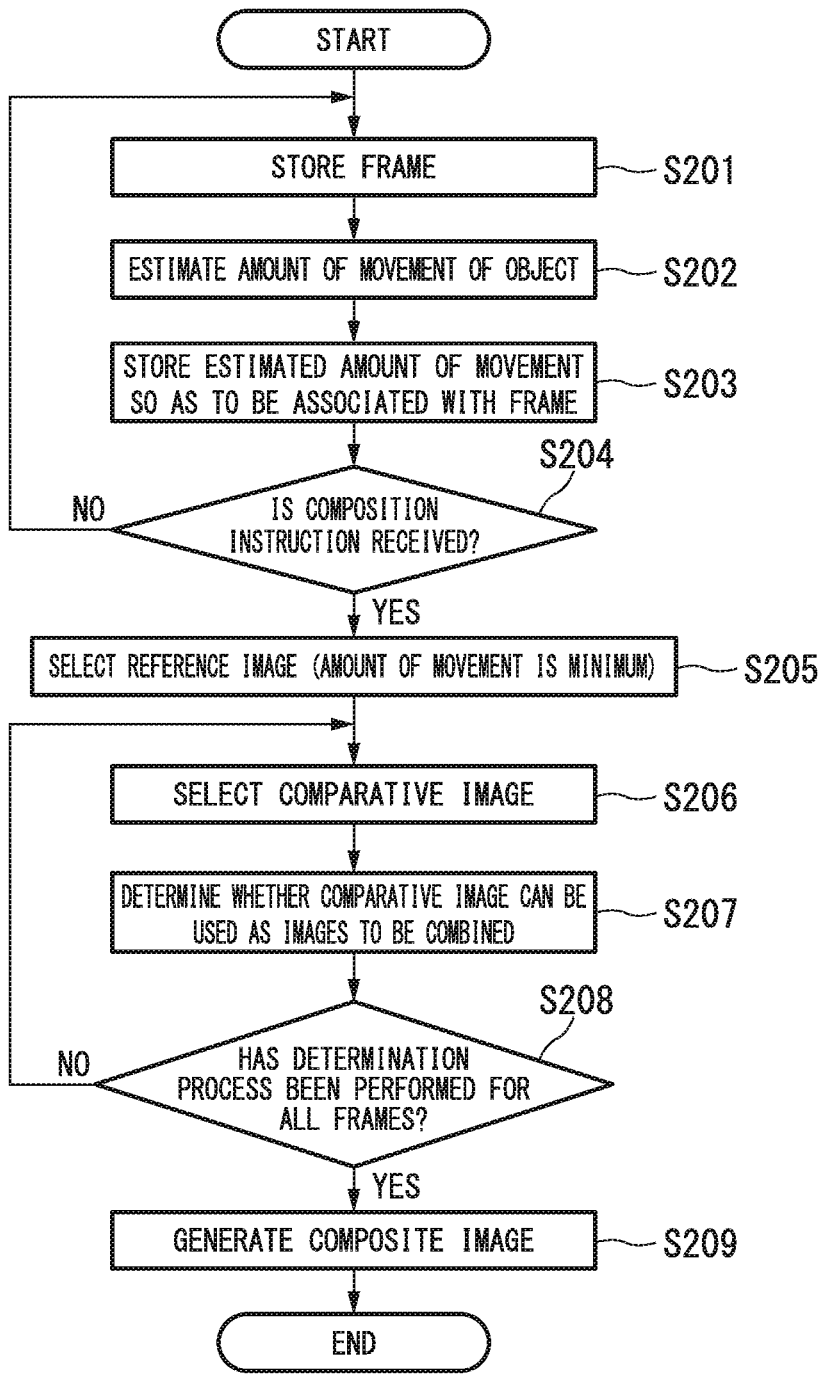
FIG. 9 is a flowchart illustrating a composite image generation process of the image processing device according to the second embodiment.

Next, a composite image generation process according to this embodiment will be described. FIG. 9 is a flowchart illustrating the composite image generation process of the image processing device 20 in this embodiment. The meaning of the amount of blur is the same as that in the first embodiment and the description thereof will not be repeated.

(Step S201) The image processing device 20 stores frames (video signals) which are input one by one from the outside in the frame memory 12. Then, the process proceeds to Step S202.

(Step S202) The movement amount estimation unit 21 estimates the amount of movement X of the object when the frame which the image processing device 20 stores in the frame memory 12 in Step S201 is captured. Then, the process proceeds to Step S203. As described above, for example, the amount of movement X of the object can be estimated by comparing the frame which is stored in the frame memory 12 in Step S201 with the previous frame.

(Step S203) The image processing device 20 stores the amount of movement X which has been estimated by the movement amount estimation unit 21 in Step S202 so as to be associated with the frame stored in Step S201. Then, the process proceeds to Step S204.

(Step S204) The composition control unit 11 determines whether a composition instruction is received. When the composition control unit 11 determines that the composition instruction is received, the process proceeds to Step S205. In the other cases, the process proceeds to Step S201.

(Step S205) The image selection unit 13 selects the reference image from a plurality of frames that are captured when the amount of movement X of the object is equal to or less than a prescribed amount of movement $X_a$ which is a threshold value. In this embodiment, first, the image selection unit 13 excludes a frame $F_0$ which is captured earliest and a frame $F_N$ which is captured latest from a plurality of frames that are captured when the amount of movement X of the object is equal to or less than the prescribed amount of movement $X_a$. Next, the image selection unit 13 selects a frame which is captured when the amount of movement X of the object is the minimum among the remaining frames, as the reference image. When there are a plurality of frames satisfying the above-mentioned conditions, a frame which is captured at the time closest to an intermediate (middle) time $t_{N/2}$ between the time $t_0$ when the oldest frame $F_0$ is captured and the time $t_N$ when the newest frame $F_N$ is captured is used as the reference image. Then, the process proceeds to Step S206.

(Step S206) The image selection unit 13 selects one comparative image from a plurality of frames which the image processing device 20 stores in the frame memory 12. Specifically, first, the image selection unit 13 excludes the frame which is selected as the reference image and the frame which has been subjected to the process in Step S207 from the frames. Next, the image selection unit 13 selects a frame which is captured at a time closest to the time when the reference image is captured from the remaining frames. When the estimated amount of movement X of the frame which the image selection unit 13 selects is less than the prescribed amount of movement $X_a$ which is a threshold value (which will be described below), the image selection unit 13 selects the selected frame as the comparative image. That is, the images to be combined are selected from a frame group in which the estimated amount of movement X is less than the prescribed amount of movement $X_a$. In other words, the image selection unit 13 reads the estimated amount of movement X which is stored so as to be associated with each frame and does not select the frame in which the estimated amount of movement X is equal to or more than the prescribed amount of movement $X_a$ as the comparative image, that is, the images to be combined. This process makes it possible to reduce the load of the following process of determining the images to be combined. Then, the process proceeds to Step S207.

(Step S207) The image selection unit 13 determines whether the comparative image selected in Step S206 can be used as the images to be combined. The process of determining whether the comparative image can be used as the images to be combined and the process of setting the images to be combined are the same as those in the first embodiment and the description thereof will not be repeated. Then, the process proceeds to Step S208.

(Step S208) The image selection unit 13 determines whether the process in Step S207 has been performed for all of the frames other than the frame selected as the standard frame and the frame in which the estimated amount of movement X is equal to or less than the prescribed amount of movement $X_a$ among a plurality of frames which the image processing device 20 stores in the frame memory 12. When the image selection unit 13 determines that the process in Step S207 has been performed for all of the frames, the process proceeds to Step S208. In the other cases, the process returns to Step S206.

(Step S209) The composition processing unit 14 composes the images to be combined set in Step S207 with the selected reference image to generate a composite image. Then, the process ends.

When the amount of movement X of the object is equal to or more than the prescribed amount of movement $X_a$, the amount of blur is greater than an allowable value in the captured image of the object. Therefore, it is preferable that the frame which is captured when the amount of movement X of the object is equal to or more than the prescribed amount of movement $X_a$ is not used as the comparative image in terms of the efficiency of the composition process. That is, it is preferable that the image processing device 20 determine whether the comparative image is used as the images to be combined using only the frame which is captured when the amount of movement X of the object is less than the prescribed amount of movement $X_a$ in terms of the efficiency of the composition process. In other words, the image processing device 20 selects the images to be combined from the frames which are captured when the amount of movement X of the object is less than the prescribed amount of movement $X_a$, which is preferable in terms of the efficiency of the composition process.

Therefore, in this embodiment, since the frame which is captured when the amount of movement X of the object is equal to or more than the prescribed amount of movement $X_a$ is not selected as the comparative image, it is possible to reduce the load of the process of determining the images to be combined.

The prescribed amount of movement $X_a$, which is a threshold value, may be predetermined or it may be arbitrarily set. For example, when a shutter speed is high, the amount of movement of the object is small even though the speed of the imaging element 104 is high. When the shutter speed is low, the amount of movement of the object is likely to be large even though the speed of the imaging element 104 is low. Therefore, when the shutter speed is high, the prescribed amount of movement $X_a$ may be set to a smaller value. When the shutter speed is low, the prescribed amount of movement $X_a$ may be set to a larger value. As such, the prescribed amount of movement $X_a$ varies depending on the shutter speed when the frame is captured. Therefore, the prescribed amount of movement $X_a$ may vary depending on the shutter speed.

It is considered that the movement of the object is caused by the movement of the imaging element and the application of this embodiment depending on the movement of the imaging element 104 will be described using the following reference examples in order to promote the understanding of this embodiment.

Figure 10:
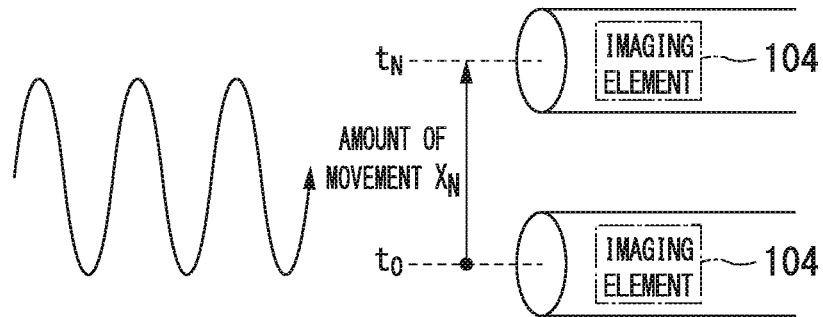
FIG. 10 is a schematic diagram illustrating an example of the movement of an imaging element in the second embodiment.
Figure 11:
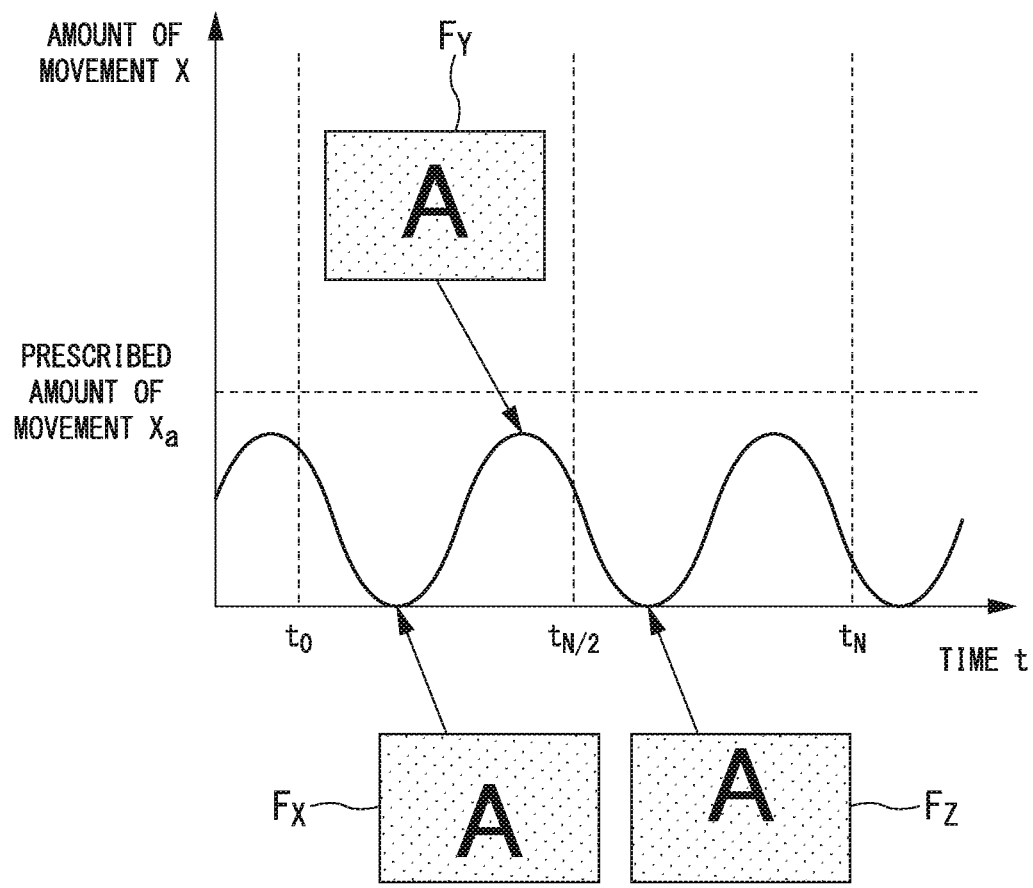
FIG. 11 is a graph illustrating an example of the relationship between a time t and the amount of movement of the imaging element in the second embodiment.

First, Reference example 1 in which the imaging element 104 regularly vibrates will be described. FIG. 10 is a schematic diagram illustrating an example of the movement of the imaging element 104. FIG. 11 is a graph illustrating the relationship between the capture time t and the amount of movement $X_N$ of the imaging element 104 during the capture of each frame when the imaging element 104 vibrates as shown in FIG. 10. In the example shown in the drawings, the imaging element 104 regularly vibrates from the time $t_0$ to the time $t_N$.

In FIG. 11, the amount of movement X of the imaging element 104 from the time $t_0$ to the time $t_N$ is constantly less than the prescribed amount of movement $X_a$. Therefore, the image selection unit 13 determines that all of the frames $F_0$ to $F_N$ captured from the time $t_0$ to the time $t_N$ can be used as the reference image and the comparative image.

Next, a comparative image selection method in Reference example 1 will be described. As described in Step S205 of FIG. 9, first, the image selection unit 13 excludes the frame $F_0$ which is captured earliest and the frame $F_N$ which is captured latest among the frames which are captured when the amount of movement X of the imaging element 104 is equal to or less than the prescribed amount of movement $X_a$. Then, the image selection unit 13 selects a frame $F_X$ and a frame $F_Z$ which are captured when the amount of movement X of the imaging element 104 is the minimum from the remaining frames and sets the selected frames as the candidate frames of the reference image.

As such, when there are a plurality of frames satisfying the comparative image selection conditions, a frame which is captured at the time closest to an intermediate time $t_{N/2}$ between the time $t_0$ when the oldest frame $F_0$ is captured and the time $t_N$ when the newest frame $F_N$ is captured is used as the reference image. Therefore, in Reference example 1, the image selection unit 13 selects the frame $F_Z$ as the reference image. A group of the frames other than the reference image (frame $F_N$) among the frames $F_0$ to $F_N$ which are captured from the time $t_0$ to the time $t_N$ is the candidates of the comparative image.

Next, the comparative image selection method will be described. In Reference example 1, as shown in FIG. 11, all of the frames, which are the candidates of the comparative image, are captured when the amount of movement is less than the prescribed amount of movement $X_a$. Therefore, all of the frames in the frame memory 12 except for the reference image can be selected as the comparative image.

Figure 12:
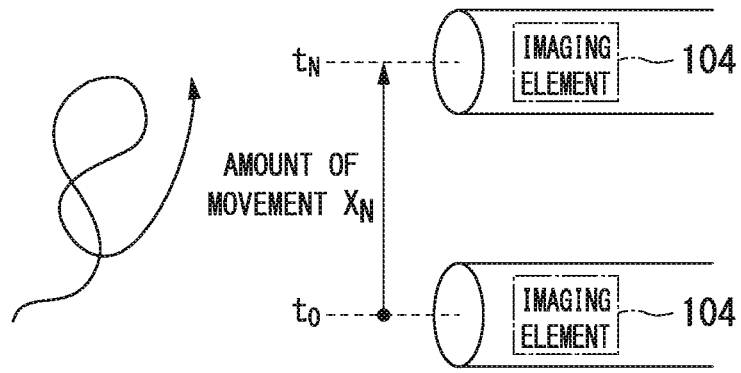
FIG. 12 is a schematic diagram illustrating an example of the movement of the imaging element in the second embodiment.
Figure 13:
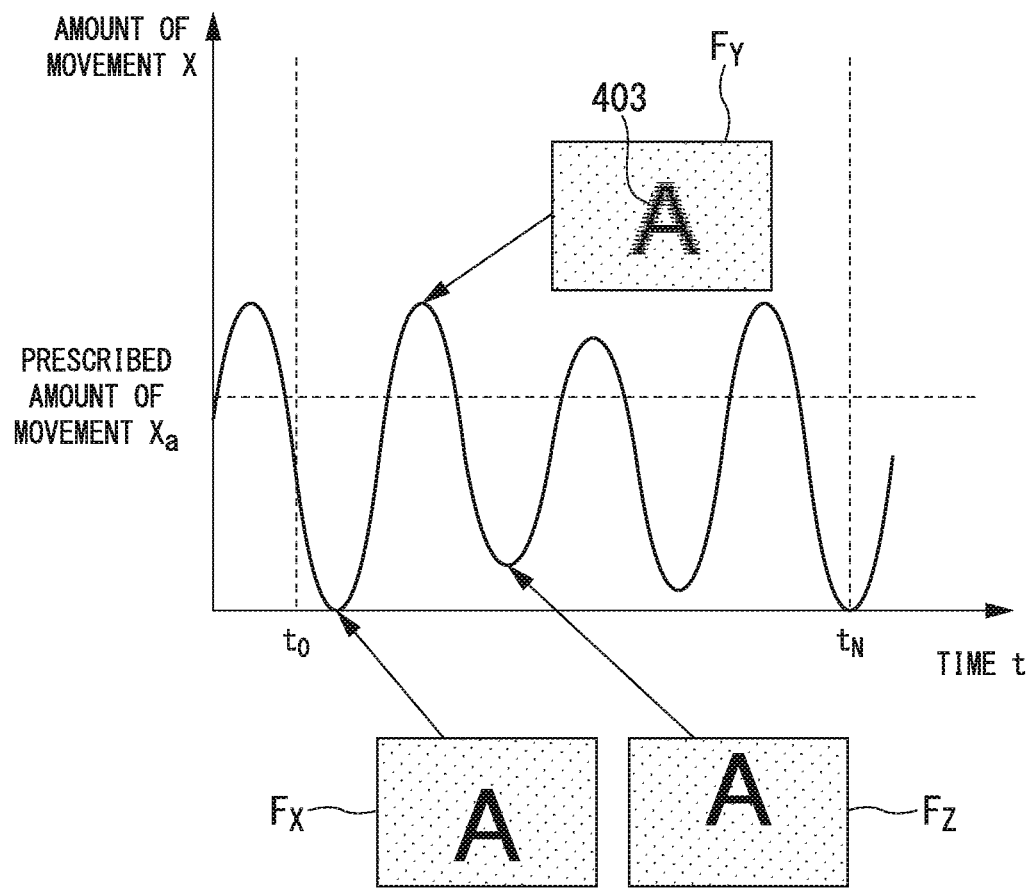
FIG. 13 is a graph illustrating an example of the relationship between the time t and the amount of movement of the imaging element in the second embodiment.

Next, Reference example 2 in which the imaging element 104 moves irregularly will be described. FIG. 12 is a schematic diagram illustrating an example of the movement of the imaging element 104. FIG. 13 is a graph illustrating the capture time t and the amount of movement X of the imaging element 104 during the capture of each frame when the imaging element 104 moves irregularly as shown in FIG. 12. In FIG. 12, the imaging element 104 moves irregularly for the period from the time $t_0$ to the time $t_N$.

In FIG. 13, there is a frame which is captured when the amount of movement of the imaging element 104 is equal to or more than the prescribed amount of movement $X_a$ the frames $F_0$ to $F_N$. For example, a frame $F_Y$ is captured when the amount of movement of the imaging element 104 is equal to or more than the prescribed amount of movement $X_a$. As shown in FIG. 13, the amount of blur of an object "A" 403 in the frame $F_Y$ is large.

For example, a frame $F_X$ and a frame $F_Z$ are captured when the amount of movement X of the imaging element 104 is less than the prescribed amount of movement $X_a$. Therefore, the image selection unit 13 determines that a group of the frames (including the frame $F_X$ and the frame $F_Z$) which are captured when the amount of movement X of the imaging element 104 is less than the prescribed amount of movement $X_a$ can be used as the reference image and the comparative image.

Next, a comparative image selection method in Reference example 2 will be described. As described in Step S205 of FIG. 9, first, the image selection unit 13 excludes the frame $F_0$ which is captured earliest and the frame $F_N$ which is captured latest among the frames which are captured when the amount of movement X of the imaging element 104 is less than the prescribed amount of movement $X_a$. Then, the image selection unit 13 selects a frame $F_X$ which is captured when the amount of movement X of the imaging element 104 is the minimum from the remaining frames and sets the selected frame as the reference image.

Next, the comparative image selection method will be described. The image selection unit 13 sequentially selects the comparative image from the frames which are captured earlier than the reference image while determining whether the estimated amount of movement X is less than the prescribed amount of movement $X_a$. In Reference example 2, as shown in FIG. 13, a frame in which the estimated amount of movement X is equal to or more than the prescribed amount of movement $X_a$ is included in a plurality of frames stored in the frame memory 12. For example, the frame is a frame $F_Y$.

The image selection unit 13 reads the estimated amount of movement X which is stored in the frame memory 12 so as to be associated with each frame, does not select the frame in which the estimated amount of movement X is equal to or more than the prescribed amount of movement $X_a$, such as the frame $F_Y$, as the comparative image, and checks the next frame or another frame. As a result, the image selection unit 13 selects, as the comparative image, only the frame in which the estimated amount of movement X is less than the prescribed amount of movement $X_a$. Therefore, in Reference example 2, the number of frames which are selected as the comparative image is less than that in Reference example 1. However, it is obvious that the frame in which the estimated amount of movement X is equal to or more than the prescribed amount of movement $X_a$ does not become the images to be combined. As a result, the process of determining whether the frame can be used as the images to be combined causes a reduction in the processing speed or an increase in processing load. Therefore, an inadequate frame is not used for the process of determining whether the frame can be used as the images to be combined and is not selected as the comparative image in a comparative image selection process which is performed before the determination process. As a result, the load of the process of determining whether the frame can be used as the images to be combined and the efficiency of the process is improved.

As described above, in this embodiment, the image selection unit 13 selects the reference image from a plurality of frames which are captured when the amount of movement X of the object is less than the prescribed amount of movement $X_a$. Preferably, the frame $F_0$ which is captured earliest and the frame $F_N$ which is captured latest are excluded from a plurality of frames which are captured when the amount of movement X of the object is less than the prescribed amount of movement $X_a$ and a frame which is captured when the amount of movement X of the object is the minimum among the remaining frames is selected as the reference image. If there are a plurality of frames which are captured when the amount of movement X of the object is the minimum, the image selection unit 13 selects, as the reference image, a frame which is captured at the time closest to the intermediate time $t_{N/2}$ between the time $t_0$ when the oldest frame $F_0$ is captured and the time $t_N$ when the newest frame $F_N$ is captured.

In addition, the image selection unit 13 selects as the comparative image, only the frame which is captured when the amount of movement X of the object is less than the prescribed amount of movement $X_a$ from the frames which are captured earlier and later with respect to the reference image. That is, the frame which is obviously improper as the images to be combined and is more than the prescribed amount of movement $X_a$ and is more equal to or more than is not used for the process of determining whether the frame can be used as the images to be combined. In other words, the image selection unit 13 does not select the frame which is obviously improper as the images to be combined. Therefore, it is possible to reduce the load of the process.

In the above-mentioned example, the image selection unit 13 determines whether all of the frames which are selected as the comparative image can be used as the images to be combined. However, the invention is not limited thereto. For example, a predetermined number of frames may be set in advance and the process may proceed to Step S209 even when there is a comparative image which has not been determined at the time the number of frames which are set as the images to be combined reaches the predetermined number of frames. In particular, in this case, the process of determining whether the frame can be used as the images to be combined is preferentially performed for the comparative image which is captured at the time close to the capture time of the reference image, which makes it possible to improve the efficiency of the composite image generation process.

The known technique may be used as the method of estimating the amount of movement of the object. For example, the movement of the object may be estimated by comparing the brightness values of two consecutive frames or by detecting the amount of movement of the imaging element using a sensor. In addition, the amount of movement of the object may be directly calculated or an element including another amount of movement which substitutes the amount of movement of the object may be calculated. For example, when the capture interval of the frame is predetermined, a speed, that is, the speed of the object or the imaging element may be calculated instead of the amount of movement.

(Third Embodiment)

Next, a third embodiment of the invention will be described with reference to the drawings. In this embodiment, the minimum total number of necessary comparative images and images to be combined (hereinafter, referred to as the number of images required for composition) is set on the basis of the amount of noise included in each frame.

Figure 14:
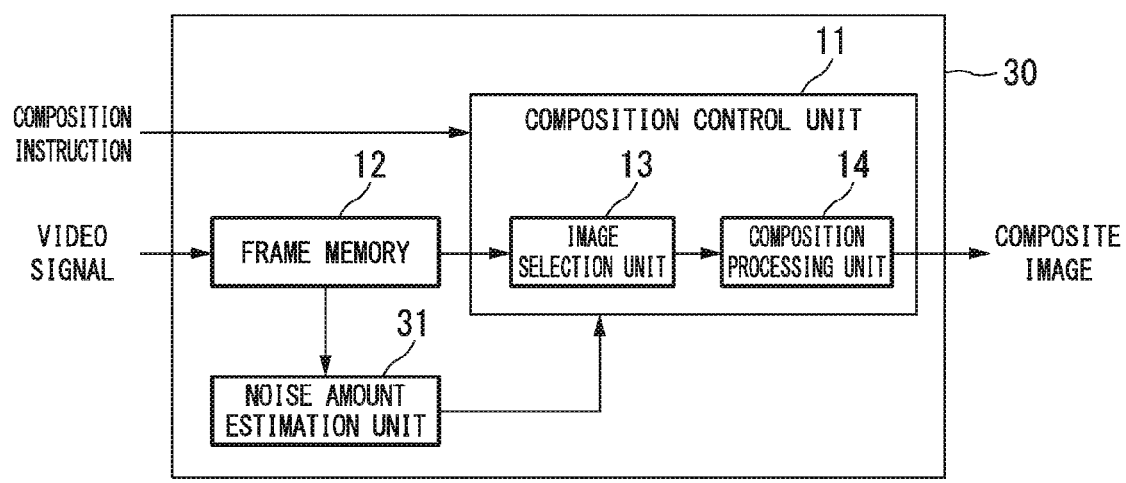
FIG. 14 is a block diagram illustrating the structure of an image processing device according to a third embodiment.

FIG. 14 is a block diagram illustrating the structure of an image processing device 30 according to this embodiment. In the example shown in FIG. 14, the image processing device 30 includes a composition control unit 11, a frame memory 12, and a noise amount estimation unit 31. The composition control unit 11 and the frame memory 12 are the same as those in the second embodiment.

The noise amount estimation unit 31 estimates the amount of noise in the frame. For example, the amount of noise is estimated on the basis of a gain value. The noise amount estimation unit 31 uses the gain value which is determined by, for example, AE control. In general, as the gain value increases, the amount of noise increases. As the gain value is reduced, the amount of noise is reduced. For example, when the gain value is large, the amount of noise estimated by the noise amount estimation unit 31 is large. When the gain value is small, the amount of noise estimated by the noise amount estimation unit 31 is small. Any method may be used as long as it can estimate the amount of noise in the frame.

In general, as the number of frames to be composed (images to be combined) increases, the amount of noise to be removed increases. Therefore, in this embodiment, when the amount of noise estimated by the noise amount estimation unit 31 is large, the image selection unit 13 increases the number of images to be combined to a large value. When the amount of noise estimated by the noise amount estimation unit 31 is small, the image selection unit 13 sets the number of images to be combined to a small value. Hereinafter, the sum of the number of images to be combined which are required in accordance with the amount of noise and the number of reference images (one reference image) is referred to as the number of images K required for composition.

Figure 15:
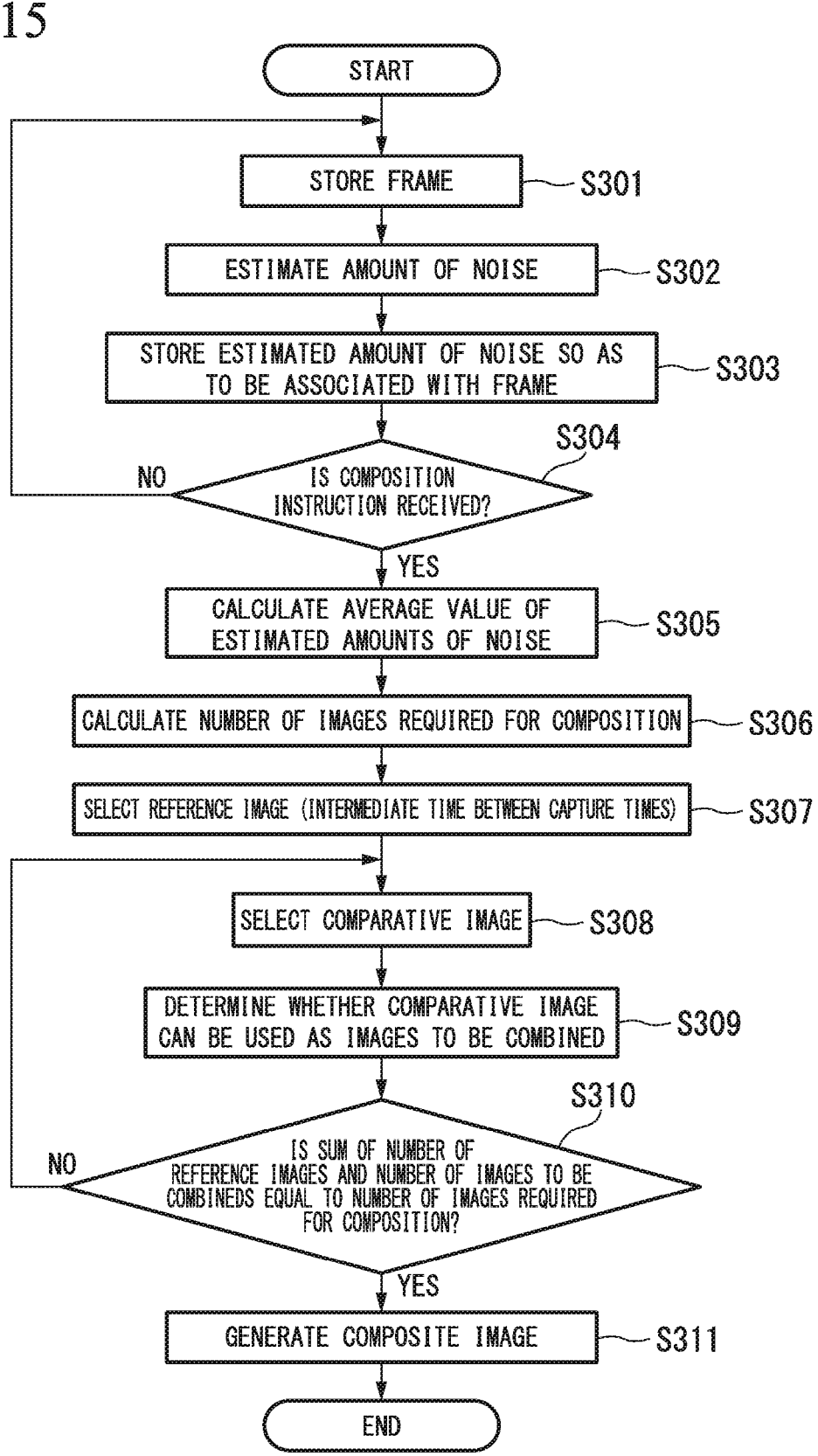
FIG. 15 is a flowchart illustrating a composite image generation process of the image processing device according to the third embodiment.

Next, a composite image generation process in this embodiment will be described. FIG. 15 is a flowchart illustrating the composite image generation process of the image processing device 30 according to this embodiment. The description of the same content as that in the first and second embodiments will not be repeated.

(Step S301) The image processing device 10 stores frames (video signals) which are input one by one from the outside in the frame memory 12.

(Step S302) The noise amount estimation unit 31 estimates the amount of noise in each frame which the image processing device 10 stores in the frame memory 12. Then, the process proceeds to Step S303.

(Step S303) The image processing device 10 stores the amount of noise which is estimated by the noise amount estimation unit 31 in Step S302 so as to be associated with each frame stored in Step S301, in the frame memory 12. Then, the process proceeds to Step S304.

(Step S304) The composition control unit 11 determines whether a composition instruction is received. When the composition control unit 11 determines that a composition instruction is received, the process proceeds to Step S305. In the other cases, the process returns to Step S301.

(Step S305) The noise amount estimation unit 31 calculates the average value of the amounts of noise of the frames stored in the frame memory 12 on the basis of the amount of noise of each frame stored in the frame memory 12. Then, the process proceeds to Step S306.

(Step S306) The image selection unit 13 calculates the number of images K required for composition on the basis of the average value of the amounts of noise calculated in Step S305. Then, the process proceeds to Step S307.

(Step S307) The image selection unit 13 selects, as the reference image, the frame which is captured at the time closest to the intermediate time between the time when the oldest frame is captured and the time when the newest frame is captured among a plurality of frames which the image processing device 10 store in the frame memory 12. This process is the same as that in Step S103 of FIG. 7. Then, the process proceeds to Step S308.

(Step S308) The image selection unit 13 selects one comparative image from the plurality of frames which the image processing device 10 store in the frame memory 12. Specifically, the comparative image is preferentially selected from the frames which are captured at the time closest to the capture time of the reference image, among the frames other than the frame which is selected as the comparative image and the frame which has been subjected to the process in Step S309. This process is the same as that in Step S206 of FIG. 9. That is, the images to be combined is preferentially selected from the frames which are captured at the time closest to the capture time of the reference image, which will be described below. Then, the process proceeds to Step S309.

(Step S309) The image selection unit 13 determines whether the comparative image selected in Step S308 can be used as the images to be combined. Since the determination method is the same as that in Step S105 of FIG. 7, the description thereof will not be repeated in this embodiment. The image selection unit 13 sets the comparative image which is determined to be used as the images to be combined as the images to be combined.

Then, the process proceeds to Step S310.

(Step S310) The image selection unit 13 determines whether the sum of the number of reference images and the number of set images to be combined is equal to the number of images K required for composition which is calculated in Step S306. When the image selection unit 13 determines that the sum is "equal to" the number of images K required for composition, the process of determining whether the comparative image can be used as the images to be combined ends even though there is a frame which has not been selected as the comparative image, in the frame memory 12. Then, the process proceeds to Step S311. When the image selection unit 13 determines that the sum is "not equal to the number of images K required for composition (the sum does not reach the number of images K required for composition)", the process returns to Step S308 and Steps S308 and S309 are repeatedly performed until the sum of the number of reference images and the number of set images to be combined reaches the number of images K required for composition.

(Step S311) The composition processing unit 14 composes the ((K−1)) images to be combined selected in Step S309 with the reference image selected in Step S307 to generate a composite image. Then, the process ends.

As described above, according to this embodiment, the image selection unit 13 selects, as the reference image, the frame which is captured at the time closest to the intermediate time between the time when the oldest frame is captured and the time when the newest frame is captured among a plurality of frames which the image processing device 10 store in the frame memory 12.

In addition, the noise amount estimation unit 31 estimates the amount of noise in each frame and calculates the average value of the amounts of noise.

The image selection unit 13 determines the number of frames (the number of images K required for composition) used to generate a composite image, on the basis of the average value of the amounts of noise calculated by the noise amount estimation unit 31. The composition process is performed using only the number of images K required for composition. Therefore, since the composition processing unit 14 generates a composite image using only the number of frames corresponding to the amount of noise, that is, only the minimum number of necessary frames, it is possible to reduce the load of the composition process.

The images to be combined selected by the image selection unit 13 is preferentially selected from the frames which are captured at the time close to the capture time of the reference image and have a relatively small amount of blur. Therefore, it is possible to improve the efficiency of the composite image generation process.

(Fourth Embodiment)

Next, a fourth embodiment of the invention will be described with reference to the drawings. In this embodiment, before a reference image is selected, a frame section including a plurality of frames (the number of frames which is less than the number of frames stored in a frame memory) is set on the basis of the estimated amount of movement X of an object. In other words, a reference image selection frame section including a plurality of frames which are consecutive in order of capture time is set on the basis of the estimated amount of movement X of the object and the reference image is selected from a plurality of frames forming the reference image selection frame section.

In this embodiment, the number of frames forming the frame section is described as the number of images K required for composition and the reference image selection frame section is described as a frame section in which the integrated value of the estimated amount of movement is the minimum.

Figure 16:
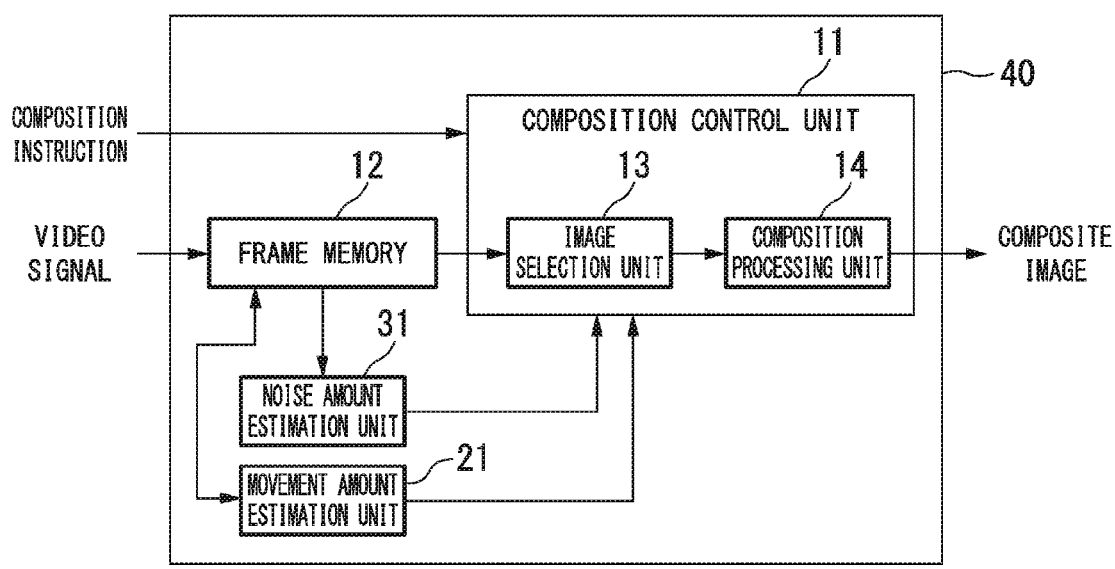
FIG. 16 is a block diagram illustrating the structure of an image processing device according to a fourth embodiment.

FIG. 16 is a block diagram illustrating the structure of an image processing device 40 according to this embodiment. In FIG. 16, the image processing device 40 includes a composition control unit 11, a frame memory 12, a movement amount estimation unit 21, and a noise amount estimation unit 31. The composition control unit 11, the frame memory 12, and the movement amount estimation unit 21 are the same as those in the second embodiment. The noise amount estimation unit 31 is the same as the noise amount estimation unit 31 in the third embodiment.

Figure 17:
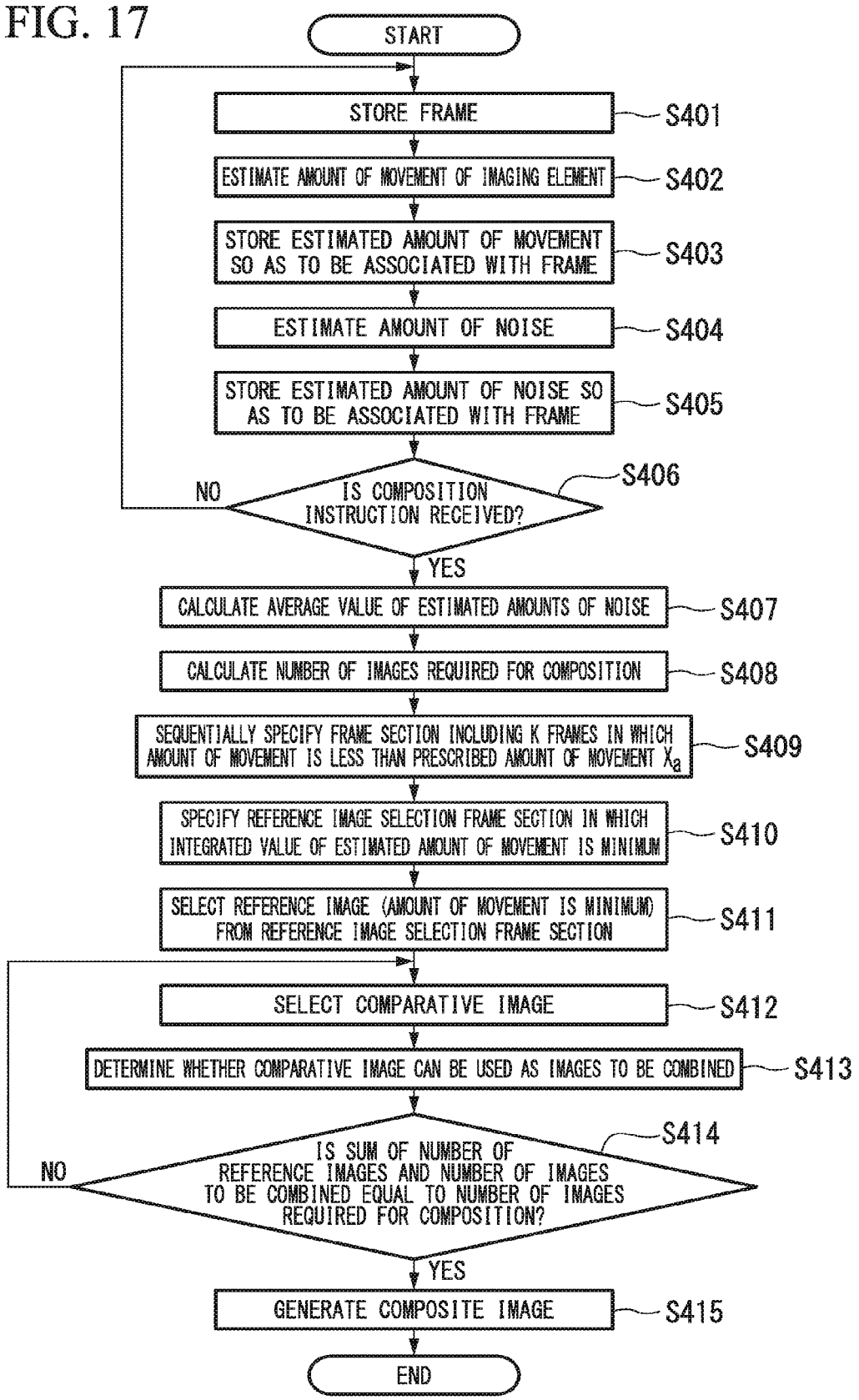
FIG. 17 is a flowchart illustrating a composite image generation process of the image processing device according to the fourth embodiment.

FIG. 17 is a flowchart illustrating a composite image generation process of the image processing device 40 in this embodiment. The description of the same content as that described in the first to third embodiments will not be repeated.

(Step S401) The image processing device 10 stores frames (video signals) which are input one by one from the outside in the frame memory 12.

(Steps S402 and S403) The movement amount estimation unit 21 estimates the amount of movement X of the object when each frame which is stored in frame memory 12 in Step S401 is captured. Then, the frame memory 12 stores the estimated amount of movement X so as to be associated with each frame. This process is the same as Steps S202 and S203 in FIG. 9.

(Step S404, S405) The noise amount estimation unit 31 estimates the amount of noise of each frame stored in the frame memory 12. Then, the frame memory 12 stores the estimated amount of noise so as to be associated with each frame. This process is the same as Steps S302 and S303 in FIG. 15.

(Step S406) The composition control unit 11 determines whether a composition instruction is received. When the composition control unit 11 determines that a composition instruction is received, the process proceeds to Step S407. In the other cases, the process returns to Step S401.

(Step S407) The noise amount estimation unit 31 calculates the average value of the amounts of noise of the frames stored in the frame memory 12 on the basis of the amount of noise of each frame stored in the frame memory 12. Then, the process proceeds to Step S408.

(Step S408) The image selection unit 13 calculates the minimum number of necessary frames required to generate a composite image, that is, the number of images K required for composition, which is the sum of the number of reference images and the number of images to be combined, on the basis of the average value of the amounts of noise which is calculated by the noise amount estimation unit 31 in Step S407. Then, the process proceeds to Step S409. This process is the same as Step S306 in FIG. 15.

(Step S409) When selecting the reference image, first, the image selection unit 13 specifies a frame section including K frames in which the amount of movement X is less than a prescribed amount of movement $X_a$, which is a threshold value, from a plurality of frames stored in the frame memory 12. The frame section is a plurality of frame groups having the oldest frame at the head. Then, the first frame in the frame section is shifted backward one by one to sequentially specify a plurality of frame sections. This process will be described with reference to FIG. 18.

Figure 18:
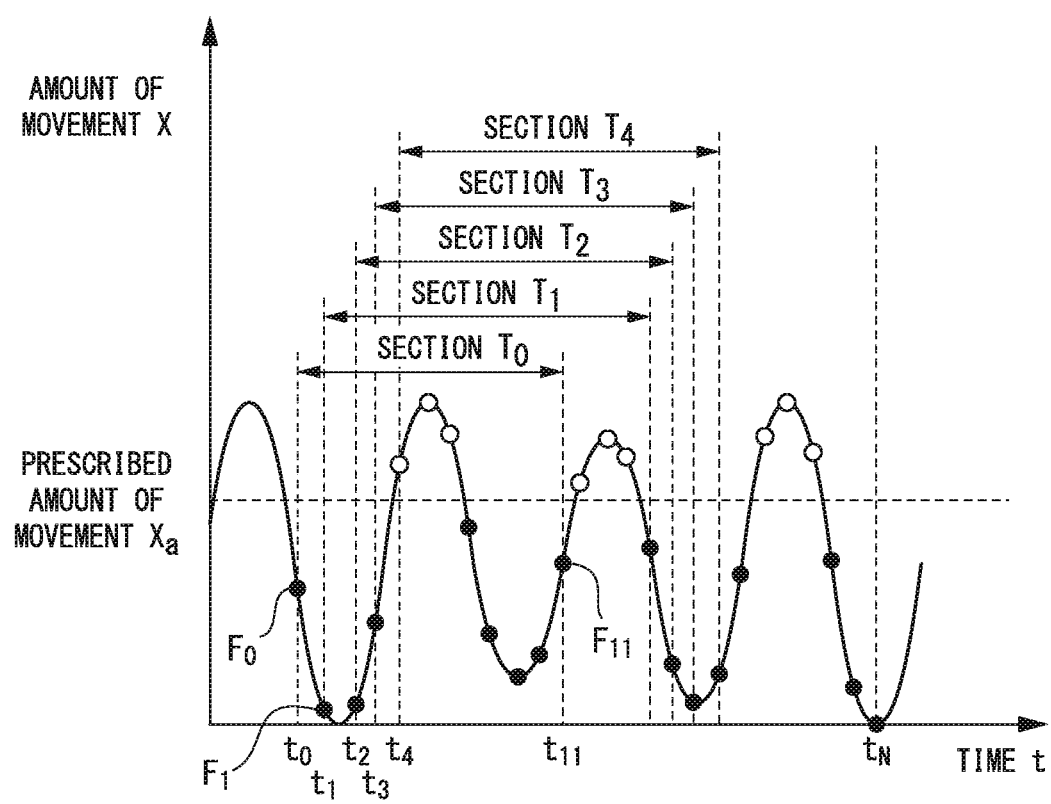
FIG. 18 is a graph illustrating an example of the relationship between a time t and the amount of movement of an imaging element in each frame stored in a frame memory in the fourth embodiment.

FIG. 18 is a graph illustrating an example of the relationship between a time t and the amount of movement X of the imaging element 104 in each frame stored in the frame memory 12. In the graph, a circle indicates a frame, a black circle indicates a frame in which the amount of movement X is less than the prescribed amount of movement $X_a$, and a white circle indicates a frame in which the amount of movement X is equal to or more than the prescribed amount of movement $X_a$.

First, the image selection unit 13 specifies a frame section $T_0$ in which the first frame is a frame $F_0$ which is captured at the earliest time $t_0$. The image selection unit 13 reads the estimated amount of movement X of the frame $F_0$, which is the first frame, from the frame memory 12 and determines whether the estimated amount of movement X is less than the prescribed amount of movement $X_a$. When the estimated amount of movement X is less than the prescribed amount of movement $X_a$, the image selection unit 13 counts the frame $F_0$ as the frame in which the estimated amount of movement X is less than the prescribed amount of movement $X_a$. When the determination process for the frame $F_0$ ends, the image selection unit 13 determines whether the estimated amount of movement X is less than the prescribed amount of movement $X_a$ for the next frame $F_1$ which is captured after the frame $F_0$. When the estimated amount of movement X is less than the prescribed amount of movement $X_a$, the image selection unit 13 counts the frame $F_1$ as the frame in which the estimated amount of movement X is less than the prescribed amount of movement $X_a$. This process is repeatedly performed until the counted number of frames reaches the number of images K required for composition. When the count result reaches the number of images K required for composition, a K-th frame is the last frame of the frame section $T_0$. In this way, the frame section $T_0$ is specified. FIG. 18 shows an example in which K is 9 and the frame section $T_0$ is from the frame $F_0$ to a frame $F_{11}$.

When the frame section $T_0$ is specified, the image selection unit 13 specifies the next frame section. The image selection unit 13 proceeds to a process of shifting the first frame to the next captured frame $F_1$ of frame $F_0$ and specifying process frame section $T_1$ having the frame $F_1$ as the first frame. Then, similarly to the operation of specifying the frame section $T_0$, the image selection unit 13 searches for a frame in which the amount of movement X is less than the prescribed amount of movement $X_a$, counts the number of frames, sets the frame as the last frame in the frame section at the time the count result reaches the number of images K required for composition, and specifies the frame section $T_1$. The image selection unit 13 repeatedly performs the specifying process of this frame section until the frame $F_N$ which is captured latest among the frames stored in the frame memory 12 becomes the last frame of the frame section. Then, the image selection unit 13 does not set, as the frame section, a frame section that does not include K frames in which the amount of movement X is less than the prescribed amount of movement $X_a$ among the frame sections. The above-mentioned process is performed to specify the frame sections $T_0$, $T_1$, $T_2$, $T_3$ . . . .

(Step S410) Then, the image selection unit 13 specifies the reference image selection frame section in which the integrated value of the amount of movement X of the object is the minimum from the specified frame sections $T_0$, $T_1$, $T_2$, $T_3$ . . . . The image selection unit 13 calculates the integrated value of the estimated amounts of movement for each frame section, on the basis of each frame in which the amount of movement X is less than the prescribed amount of movement $X_a$ in each frame section. Then, the image selection unit 13 performs the calculation process for all of the frame sections $T_0$, $T_1$, $T_2$, $T_3$ . . . which are obtained in Step S409. Then, the image selection unit 13 specifies, as the reference image selection frame section, the frame section in which the calculated integrated value of the amounts of movement is the minimum.

Figure 19:
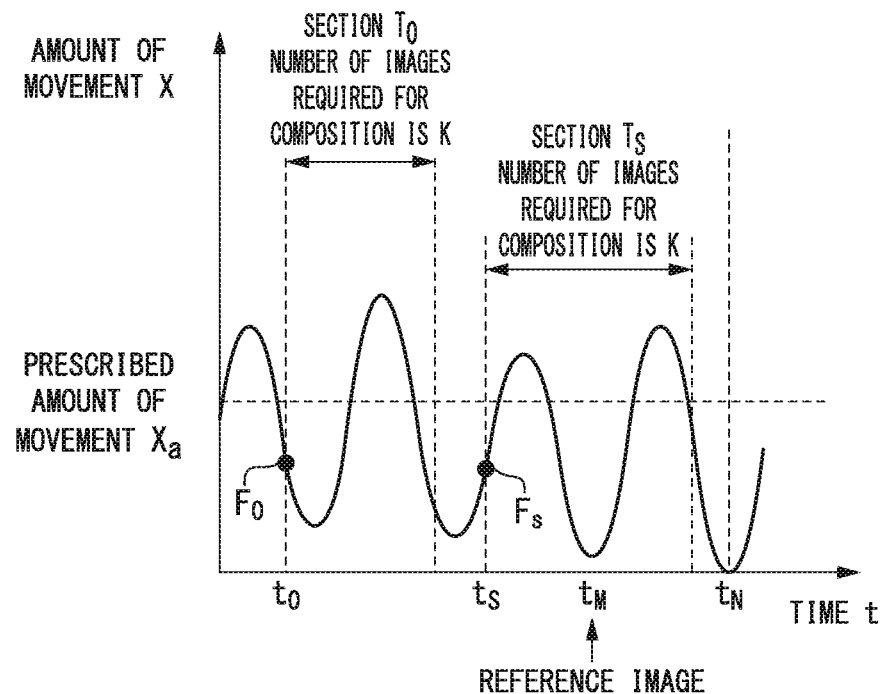
FIG. 19 is a graph illustrating an example of the relationship between the time t and the amount of movement of the imaging element in the fourth embodiment.

FIG. 19 is a graph illustrating only the frame section $T_0$ having the frame $F_0$ as the first frame and the frame section $T_s$ having the frame $F_s$ as the first frame among a plurality of frame sections.

The amount of the integration of the amount of movement in the frame section $T_s$ is less than the amount of integration of the amount of movement in the frame section $T_0$. In this case, the image selection unit 13 specifies the frame section $T_s$ as the reference image selection frame section.

(Step S411) The image selection unit 13 selects the reference image from a plurality of frames included in the specified reference image selection frame section. Specifically, first, the image selection unit 13 excludes the frame which is captured earliest and the frame which is captured latest in the reference image selection frame section from the candidates of the reference image. Then, the image selection unit 13 selects the frame which is captured when the estimated amount of movement X of the object is the minimum from the remaining frames, as the reference image.

Figure 20:
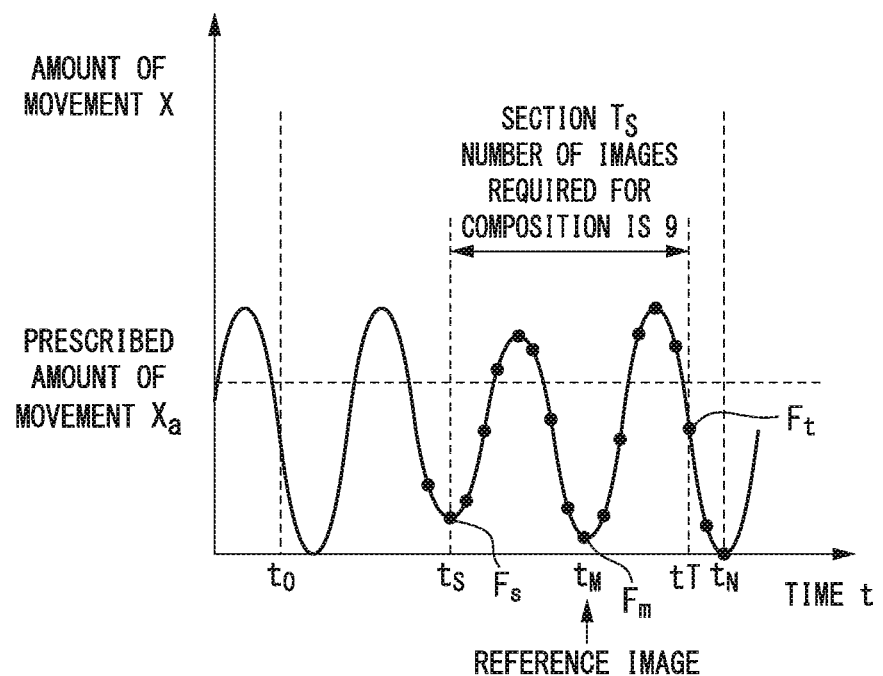
FIG. 20 is a schematic diagram illustrating an example of the selection of a reference image in the fourth embodiment.

This process will be described with reference to FIG. 20. In the graph shown in FIG. 20, a frame is indicated by a black circle in the reference image selection frame section $T_s$ shown in FIG. 19. First, the image selection unit 13 excludes the first frame $F_s$ and the last frame $F_t$ in the reference image selection frame section $T_s$ from the comparative image candidates. Then, the image selection unit 13 reads the estimated amount of movement relative to the remaining frames in the reference image selection frame section $T_s$ from the frame memory 12 and searches for the frame in which the estimated amount of movement is the minimum.

Then, the image selection unit 13 selects, as the reference image, a frame $F_m$ which is captured at a time $t_m$.

(Step S412) After the reference image selection process ends, the image selection unit 13 proceeds to a comparative image selection process. First, the image selection unit 13 excludes the standard frame and the frame which has been subjected to the process in Step S413, which will be described below, from a plurality of frames stored in the frame memory 12. Then, the image selection unit 13 selects, from the remaining frames, the frame which is captured at the time closest to the capture time of the reference image as a comparative image candidate. Then, when the amount of movement X is less than the prescribed amount of movement $X_a$ in the frame which is selected as the comparative image candidate, the image selection unit 13 selects the selected frame as the comparative image. When the amount of movement is equal to or more than the prescribed amount of movement $X_a$ in the frame which is selected as the comparative image candidate, the image selection unit 13 determines that the frame is not the comparative image and selects the next frame which is captured at the time close to the capture time of the reference image as the comparative image candidate. This process is the same as Step S206 in FIG. 9.

The image selection unit 13 may end the comparative image selection process when the frame selected as the comparative image candidate is determined not to be the comparative image, the next selected comparative image candidate is determined not to be the comparative image, and the comparative image candidate is determined not to be the comparative image a prescribed consecutive number of times as a result and proceed to Step S415. The prescribed number of times may be predetermined or it may be arbitrarily set.

In this embodiment, the selected comparative image is preferentially selected from the frames in the previously obtained reference image selection frame section. However, the comparative image may be selected from the frames outside the reference image selection frame section. The image selection unit 13 selects all of the frames in the reference image selection frame section as the comparative image and determines whether the comparative image is used as the images to be combined. As a result, when the number of frames which are set as the images to be combined does not reach the number of images K required for composition including the reference image, the image selection unit 13 selects, as the comparative image, the frame which is outside the reference image selection frame section, which is captured at the time closest to the capture time of the reference image, and of which the amount of movement is less than the prescribed amount of movement $X_a$. Then, the process proceeds to Step S413.

(Step S413) The image selection unit 13 determines whether the comparative image selected in Step S412 can be used as the images to be combined. When it is determined that the selected comparative image can be used as the images to be combined, the image selection unit 13 sets the frame which is selected as the comparative image as the images to be combined. The determination method is the same as that in Step S207 in FIG. 9. Then, the process proceeds to Step S414.

When it is determined a prescribed consecutive number of times that the frame selected as the comparative image is not available as the images to be combined, the image selection unit 13 may end the process of determining whether the comparative image can be used as the images to be combined and proceed to Step S415. The prescribed number of times may be predetermined or it may be arbitrarily set.

(Step S414) The image selection unit 13 determines whether the sum of the number of a reference image (single) and the number of set images to be combined is equal to the number of images K required for composition calculated in Step S408. When the image selection unit 13 determines that the sum is "equal to" the number of images K required for composition, the process proceeds to Step S415. In the other cases, the process returns to Step S412 and Steps S412 and S413 are repeatedly performed until the sum of the number of reference images and the number of set images to be combined reaches the number of images K required for composition.

(Step S415) The composition processing unit 14 composes ((K-1)) frames which are set as the images to be combined with the reference image to generate a composite image.

As described above, according to this embodiment, the reference image is selected from a plurality of frames in which the amount of movement of the object is the minimum in the frame section (reference image selection frame section) and the images to be combined is preferentially set from the frames which are captured at the time close to the capture time of the reference image. Therefore, it is possible to preferentially set the images to be combined with a small amount of blur or a small amount of movement relative to the reference image. As a result, it is possible to generate a composite image using the frames which are suitable for composition and thus to improve the efficiency of the composition processing.

(Fifth Embodiment)

Next, a fifth embodiment of the invention will be described with reference to the drawings. In this embodiment, a reference image is selected on the basis of the amount of movement of the object to be estimated by a movement amount estimation unit 21, which will be described below.

Figure 21:
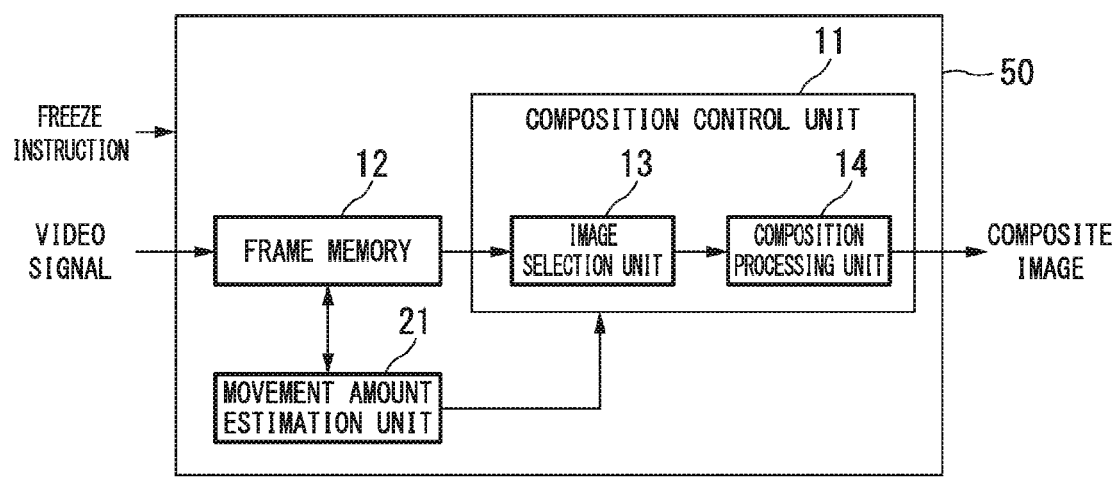
FIG. 21 is a block diagram illustrating the structure of an image processing device according to a fifth embodiment.

FIG. 21 is a block diagram illustrating the structure of an image processing device 50 according to this embodiment. In FIG. 21, the image processing device 50 includes a composition control unit 11, a frame memory 12, and the movement amount estimation unit 21. The composition control unit 11 and the frame memory 12 are the same as those in the first embodiment. The movement amount estimation unit 21 estimates the amount of movement X of the object.

In this embodiment, frame processing has been described. However, if interlaced processing is performed, the amount of movement X of the object may be estimated using a newly input interlace image and an interpolated image based on a previously input interlace image.

Figure 22:
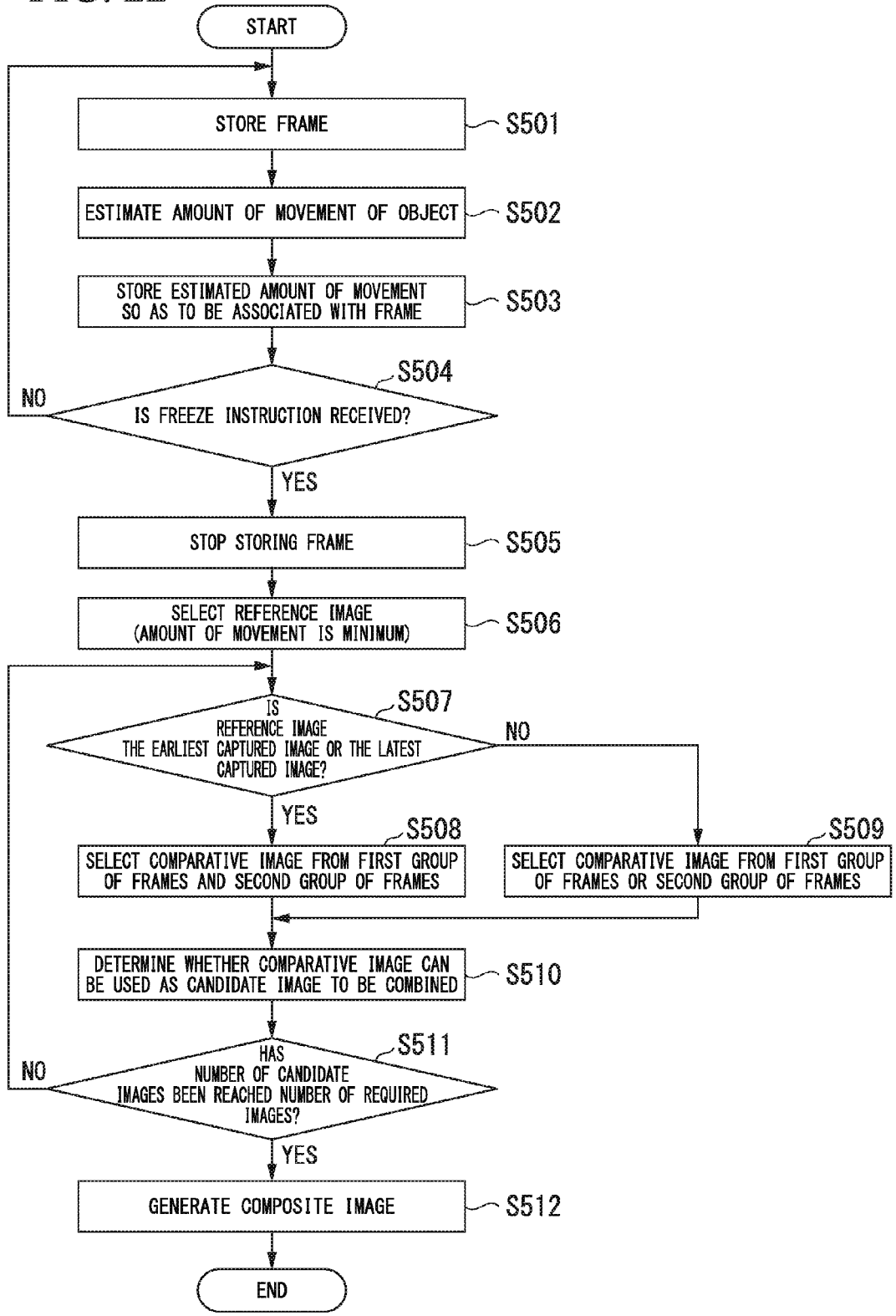
FIG. 22 is a flowchart illustrating a composite image generation process of the image processing device according to the fifth embodiment.

Next, a composite image generation process according to this embodiment will be described. FIG. 22 is a flowchart illustrating the composite image generation process of the image processing device 50 in this embodiment. The meaning of the amount of blur is the same as that in the first embodiment and the description thereof will not be repeated.

(Step S501) The image processing device 50 stores frames (video signals) which are input one by one to the frame memory 12. Then, the process proceeds to Step S502.

(Step S502) The movement amount estimation unit 21 estimates the amount of movement X of the object if the frame which the image processing device 50 stores in the frame memory 12 in Step S501 is captured. Then, the process proceeds to Step S503. As described above, for example, the amount of movement X of the object can be estimated by comparing the frame which is stored by the image processing device 50 in the frame memory 12 in Step S501 with the previous one frame.

(Step S503) The image processing device 50 stores the amount of movement X which has been estimated by the movement amount estimation unit 21 in Step S502 so as to be associated with the frame stored in Step S201. Then, the process proceeds to Step S504.

(Step S504) The image processing device 50 determines whether a freeze instruction, which is used for instructing to display a still image on a monitor (not shown), is received. If the image processing device 50 determines that the freeze instruction is received, the process proceeds to Step S505. In the other cases, the process proceeds to Step S501.

(Step S505) The image processing device 50 stops storing the frames (video signals) in the frame memory 12.

(Step S506) The image selection unit 13 selects the reference image from a plurality of frames that are stored in the frame memory 12. In this embodiment, the image selection unit 13 selects a frame in which the amount of movement X of the object is the smallest among the plurality of frames stored in the frame memory 12, as the reference image. Then, the process proceeds to Step S507.

(Step S507) The image selection unit 13 confirms the capture time of each of the frames stored in the frame memory 12, including the selected reference image. Then, the image selection unit 13 determines whether the reference image is an earliest captured frame (oldest frame), or a latest captured frame (newest frame) among the plurality of frames stored in the frame memory 12. Next, the process proceeds to Step S508 if the reference image is neither the earliest captured frame nor the latest captured frame. The process proceeds to Step S509 if the reference image is either the earliest captured frame or the latest captured frame.

(Step S508) The image selection unit 13 selects frames from both of a first group of frames and a second group of frames as comparative images in order from a closest capture time to a capture time of the reference image to a farthest capture time to the capture time of the reference image. The first group of frames is constituted by frames captured earlier than the reference image. The second group of frames is constituted by frames captured later than the reference image. That is, the reference image is sandwiched by the selected comparative images, and the comparative images can be selected from the group of frames captured earlier than the reference image and the group of frames captured later than the reference image.

The comparative images may be alternately read out from the first group of frames and the second group of frames.

(Step S509) The image selection unit 13 selects frames from one of a first group of frames or a second group of frames as a comparative image in order from a closest capture time to a capture time of the reference image to a farthest capture time to the capture time of the reference image. The first group of frames is constituted by the frames which are captured earlier than the reference image. The second group of frames is constituted by the frames which are captured later than the reference image. For example, the image selection unit 13 selects the comparative images only from the first group of frames, if the latest captured frame among the plurality frames stored in the frame memory 12 is determined to be the reference image. On the other hand, for example, the image selection unit 13 selects the comparative images only from the second group of frames, if the earliest captured frame is determined to be the reference image.

(Step S510) The image selection unit 13 determines whether the comparative images selected in Step S508 or Step S509 can be used as the candidate images to be combined with the reference image. The process of determining whether the comparative image can be used as the candidate images to be combined and the process of setting the images to be combined are the same as those described in the first embodiment and the description thereof will not be repeated. Then, the process proceeds to Step S511.

(Step S511) The image selection unit 13 counts the number of the candidate images to be combined and confirms whether the number of the candidate images reaches a predetermined number of required images.

If the image selection unit 13 confirms that the number of the candidate images to be combined has reached the number of required images, even there is a comparative image which has not been subjected to the process of determining whether the comparative image can be used as the candidate image to be combined, the process proceeds to Step S512. On the other hand, if the number of the candidate images to be combined has not reached the number of required images, the process returns to Step S507.

The number of required images may be a predetermined value and may be calculated by the same method as that of the number of images K required for composition as described in the above-mentioned embodiments.

The image selection unit 13 may end the process of determining whether the comparative images are used as the candidate image to be combined, if it is determined that the selected comparative images cannot be used as the candidate images to be combined with the reference image by the image selection unit 13 for the predetermined number of times consecutively.

(Step S512) The composition processing unit 14 composes the candidate images to be combined set in Step S510 with the selected reference image to generate a composite image. Then, the process ends.

In the present embodiment, the candidate image to be combined can be selected from both of the first group of frames that is constituted by the frames captured earlier than the reference image and the second group of frames that is constituted by the frames captured later than the reference image, if the reference image is determined neither the earliest captured frame nor the latest captured frame.

(Sixth Embodiment)

Figure 23:
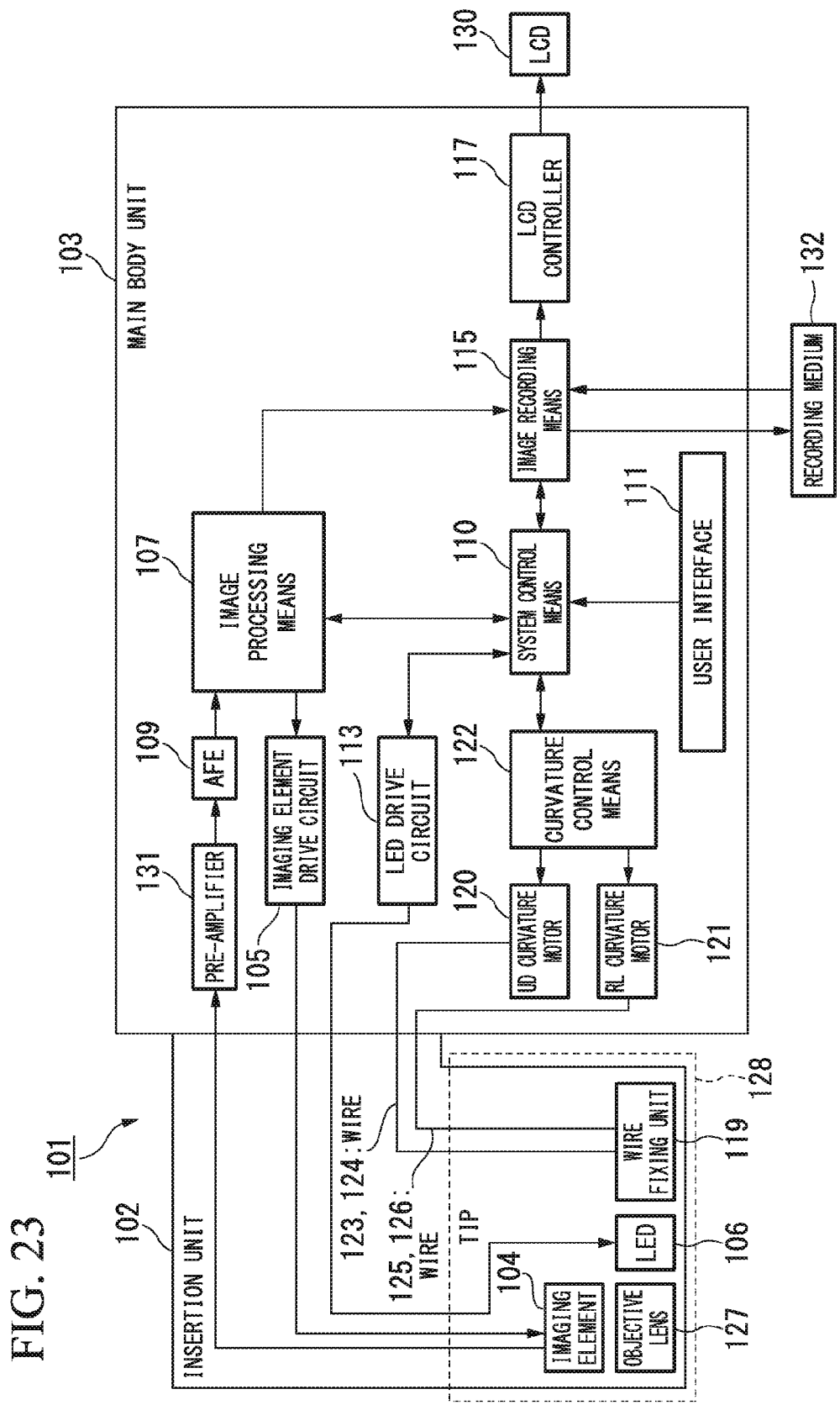
FIG. 23 is a block diagram illustrating the structure of an endoscope apparatus according to a sixth embodiment.

Next, a sixth embodiment of the invention will be described with reference to the drawings. FIG. 23 is a block diagram illustrating the structure of an endoscope apparatus according to this embodiment. In the example shown in FIG. 23, an endoscope apparatus 101 includes an elongated insertion unit 102, a main body unit 103, and a liquid crystal display (LCD) 130. In addition, a recording medium 132 can be attached to the main body unit 103. For example, still images or moving images which are captured by the endoscope apparatus 101 can be recorded on the recording medium 132.

The insertion unit 102 includes an objective lens 127, an imaging element (charge coupled device (CCD)) 104, a light emitting diode (LED) 106, and a wire fixing unit 119. The objective lens 127, the imaging element 104, the LED 106, and the wire fixing unit 119 are arranged at a tip 128 (endoscope tip) of the insertion unit 102.

The main body unit 103 includes an imaging element drive circuit 105, a pre-amplifier 131, image processing means 107, an analog front end (AFE) 109, system control means 110, a user interface 111, an LED drive circuit 113, UD (up/down) curvature motor 120, an RL (right/left) curvature motor 121, curvature control means 122, image recording means 115, and an LCD controller 117. In addition, the endoscope apparatus 101 includes four wires 123 to 126 for curving the tip 128 of the insertion unit 102 in all directions.

The user interface 111 includes, for example, a switch or a joystick for curving the tip of the endoscope, receives an instruction input from the user, and outputs a signal corresponding to the received input to the system control means 110. Examples of the instruction from the user include an instruction for a zoom ratio, an instruction for the brightness of the image to be captured, an instruction to turn on and off the LED 106, an instruction to curve the tip 128 of the insertion unit 102, an instruction to record images on the recording medium 132, and an instruction to display images o the LCD 130.

The system control means 110 controls each unit of the endoscope apparatus 101 such that a process based on the signal input from the user interface 111 is performed. For example, when the user interface 111 receives an input indicating the zoom ratio or an input indicating the brightness of the image to be captured, the system control means 110 controls the image processing means 107 such that a process based on the input received by the user interface 111 is performed. In addition, when the user interface 111 receives an input indicating the turn-on and turn-off of the LED 106, the system control means 110 controls the LED drive circuit 113 such that a process based on the input received by the user interface 111 is performed. When the user interface 111 receives an input indicating the curving of the tip 128 of the insertion unit 102, the system control means 110 controls the curvature control means 122 such that a process based on the input received by the user interface 111 is performed. When the user interface 111 receives an input indicating the recording of images on the recording medium 132 or an input indicating the display of images on the LCD 130, the system control means 110 controls the image recording means 115 such that a process based on the input received by the user interface 111 is performed.

The wire fixing unit 119 fixes the four wires 123 to 126 for curving the tip 128 of the insertion unit 102 in all directions. Among the four wires 123 to 126, two wires 123 and 124 for curving the tip 128 of the insertion unit 102 in the up-down direction are connected to the UD curvature motor 120. In addition, two wires 125 and 126 for curving the tip 128 of the insertion unit 102 in the left-right direction are connected to the RL curvature motor 121.

The UD curvature motor 120 and the RL curvature motor 121 are connected to the curvature control means 122. The curvature control means 122 is connected to the system control means 110. The curvature control means 122 controls the driving of the UD curvature motor 120 on the basis of a curvature instruction signal related to the up-down direction which is input from the system control means 110 and controls the driving of the RL curvature motor 121 on the basis of a curvature instruction signal related to the left-right direction which is input from the system control means 110. The UD curvature motor 120 draws the two wires 123 and 124 to curve the tip 128 of the insertion unit 102 in the up-down direction under the control of the curvature control means 122. In addition, the RL curvature motor 121 draws the two wires 125 and 126 to curve the tip 128 of the insertion unit 102 in the left-right direction under the control of the curvature control means 122.

According to this structure, when the user tilts the joystick of the user interface 111 in the up-down direction, the system control means 110 transmits the curvature instruction signal related to the up-down direction to the curvature control means 122. The curvature control means 122 controls the driving of the UD curvature motor 120 on the basis of the received curvature instruction signal and draws the wires 123 and 124 connected to the UD curvature motor 120. In this way, the endoscope apparatus 101 can curve the tip 128 of the insertion unit 102 in the up-down direction. The tip is curved in the left-right direction by the same method as described above. When the user tilts the joystick in the left-right direction, the system control means 110 transmits the curvature instruction signal related to the left-right direction to the curvature control means 122. The curvature control means 122 controls the driving of the RL curvature motor 121 on the basis of the received curvature instruction signal and draws the wires connected to the RL curvature motor 121. In this way, the endoscope apparatus 101 can curve the tip 128 of the insertion unit 102 in the left-right direction.

The LED 106 is connected to the LED drive circuit 113 through a cable. The LED drive circuit 113 is connected to the system control means 110. The LED drive circuit 113 controls the turn-on and turn-off of the LED 106 on the basis of an LED turn-on signal input from the system control means 110. The LED 106 is turned on and off under the control of the LED drive circuit 113.

The objective lens 127 forms an object image illustrated by the LED 106 on a light receiving surface of the imaging element 104. The imaging element 104 is connected to the imaging element drive circuit 105 and the pre-amplifier 131 through a combined coaxial cable. The imaging element drive circuit 105 receives a timing signal for driving the imaging element 104 from a timing generator which is provided in the image processing means 107. Then, the imaging element drive circuit 105 performs a drive process corresponding to the length of a transmission path (the length of the combined coaxial cable) to the imaging element 104 for the received timing signal and transmits the processed timing signal as an imaging element driving signal to the imaging element 104.

The imaging element 104 converts the light focused on the light receiving surface into an electric signal on the basis of the timing of the transmitted imaging element driving signal and outputs the converted electric signal as an imaging element output signal. The imaging element output signal output from the imaging element 104 is input to the pre-amplifier 131 through the combined coaxial cable. The pre-amplifier 131 amplifies the imaging element output signal in order to compensate for a signal level which is attenuated by transmission through the combined coaxial cable. The imaging element output signal amplified by the pre-amplifier 131 is input to the AFE 109. The AFE 109 performs a correlated double sampling (CDS) process, an auto gain control (AGC) process, or an analog/digital (AD) conversion process for the input imaging element output signal. The imaging element output signal (frame) processed by the AFE 109 is input to the image processing means 107.

The image processing means 107 includes at least one of the image processing device 10 according to the first embodiment, the image processing device 20 according to the second embodiment, the image processing device 30 according to the third embodiment, the image processing device 40 according to the fourth embodiment, and the image processing device 50 according to the fifth embodiment. The image processing means 107 generates a composite image using the input imaging element output signal (frame) and removes noise, under the control of the system control means 110. The image processing means 107 according to this embodiment generates the composite image using any one of a plurality of generation methods according to the first to fifth embodiments, according to the image processing devices 10, 20, 30, 40, and 50 provided therein.

The image processing means 107 may perform various kinds of camera signal processing, such as white balance correction, gamma correction, contour correction, electronic zoom processing, color correction, contrast correction, and AE control. In addition, the image processing means 107 outputs the generated composite image as image data to the image recording means 115.

The image recording means 115 outputs the input image data to the LCD controller 117. In addition, the image recording means 115 performs a freeze process of displaying a still image on the LCD 130. The image recording means 115 compresses the input image data with an encoder and records the image data as still image data or moving image data on the recording medium 132. This image recording operation is performed on the basis of the input from the user interface 111 when the system control means 110 transmits a recording signal to the image recording means 115 and the image recording means 115 receives the recording signal.

The endoscope apparatus 101 captures a still image when image recording is performed after the image recording means 115 performs the freeze process and captures a moving image when image recording is performed without the freeze process. The image recording means 115 performs an image reproduction operation of reading still image data or moving image data from the recording medium 132, decompressing the data, and outputting the decompressed data to the LCD controller 117. This image reproduction operation is performed when the system control means 110 receives an image display signal from the user interface 111.

The LCD controller 117 performs image processing (for example, gamma correction, scaling, and RGB conversion) which is most suitable for the connected LCD 130 for various kinds of image data input from the image recording means 115 and outputs the processed image data to the LCD 130. The LCD 130 displays an image on the basis of the input image data.

As described above, the image processing means 107 of the endoscope apparatus 101 includes at least one of the image processing device 10 according to the first embodiment, the image processing device 20 according to the second embodiment, the image processing device 30 according to the third embodiment, the image processing device 40 according to the fourth embodiment, and the image processing device 50 according to the fifth embodiment. Therefore, the image processing means 107 can generate a composite image using the frame which is more suitable for composition among the frames captured by the imaging element 104 of the endoscope apparatus 101. In addition, the image processing means 107 can obtain the same effect as the image processing devices 10, 20, 30, 40, and 50, according to the image processing devices 10, 20, 30, 40, and 50 provided therein.

A plurality of embodiments of the invention have been described above with reference to the drawings. However, the detailed structure is not limited to the plurality of embodiments and the invention also includes, for example, the structure which is designed without departing from the scope and spirit of the invention.

All or some of the functions of each unit provided in the image processing devices 10, 20, 30, 40, and 50 according to the above-described embodiments may be implemented by recording a program for implementing the functions on a computer-readable recording medium and allowing a computer system to reading the program recorded on the recording medium and to execute the program. The term "computer system" includes an OS and hardware, such as peripheral devices.

Typically, examples of the "computer-readable recording medium" include portable media, such as a flexible disk, a magneto-optical disk, a ROM, and a CD-ROM, and a recording unit, such as a hard disk provided in the computer system. However, the computer-readable recording medium is not necessarily limited thereto.

In addition, the following means may be used instead of the "computer-readable recording medium". For example, the computer-readable recording medium may be a medium that dynamically stores a program for a short period of time, such as a communication line used when a program is transmitted through a network such as the Internet or a communication line such as a telephone line. In addition, in this case, the computer-readable recording medium may be a medium that stores a program for a predetermined period of time, such as a volatile memory provided in a computer system serving as a server or client. Furthermore, the program may be executed to implement some of the above-mentioned functions. Further, the above-mentioned functions may be implemented by combinations of all programs recorded on the computer system.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. An image processing device comprising:
   a memory configured to store a plurality of captured images; and
   a processor comprising hardware, wherein the processor is configured to:
      select a reference image from among the plurality of captured images stored in the memory;
      select candidate images to be combined with the reference image from a first group of images and a second group of images among the plurality of captured images, wherein the reference image is neither the earliest captured image nor the latest captured image stored in the memory, wherein:
         the first group of images is captured earlier than the reference image; and
         the second group of images is captured later than the reference image; and
      combine the candidate images with the reference image to generate a composite image,
   wherein the processor is configured to select the candidate images to be combined with the reference image by:
      selecting images from the first group of images and the second group of images in order from an image having a capture time closest to a capture time of the reference image to an image having a capture time farthest from the capture time of the reference image, and
      determining whether the images selected can be used as the candidate images to be combined with the reference image in the order in which the images from the first group of images and the second group of images are selected.

2. The image processing device according to claim 1, wherein the processor is configured to:
   estimate an amount of movement of an object in one or more images among the plurality of captured images; and
   select the reference image based on the amount of movement estimated.

3. The image processing device according to claim 2, wherein the processor is configured to select an image in which the estimated amount of movement is the minimum as the reference image.

4. The image processing device according to claim 1, wherein the processor is configured to end the selecting of the candidate images to be combined with the reference image in response to determining that a number of selected images reaches a predetermined number of images required to be combined with the reference image.

5. The image processing device according to claim 1, wherein the processor is configured to end the selecting of the candidate images to be combined with the reference image in response to determining that a predetermined number of consecutive images are not selected as the candidate images to be combined with the reference image during the determining of whether the images selected can be used as the candidate images to be combined.

6. A method for processing a plurality of images stored in a memory, the method comprising:
   selecting a reference image from among the plurality of images stored in the memory;
   selecting candidate images to be combined with the reference image from a group of images captured earlier than the reference image and another group of images captured later than the reference image among the plurality of images, wherein the reference image is neither the earliest captured image nor the latest captured image among the plurality of images stored in the memory; and
   combining the candidate images with the reference image to generate a composite image,
   wherein selecting the candidate images to be combined with the reference image comprises determining whether images selected from the plurality of images stored in the memory can be used as the candidate images, in order from an image with a capture time closest to a capture time of the reference image to an image with a capture time farthest from the capture time of the reference image.

7. A non-transitory computer-readable recording medium storing a program causing a computer to perform:
   selecting a reference image from among a plurality of images stored in a memory;
   selecting candidate images to be combined with the reference image from a first group of images captured earlier than the reference image and a second group of images captured later than the reference image from among the plurality of images, in order from an image having a capture time closest to a capture time of the reference image to an image having a capture time farthest from the capture time of the reference image, wherein the reference image is neither the earliest captured image nor the latest captured image among the plurality of images stored in the memory; and combining the candidate images with the reference image to generate a composite image,
wherein selecting the candidate images to be combined with the reference image comprises determining whether images selected from the plurality of images stored in the memory can be used as the candidate images to be combined with the reference image.

* * * * *